(12) United States Patent
Martin et al.

(10) Patent No.: US 10,413,344 B2
(45) Date of Patent: Sep. 17, 2019

(54) DEVICES AND METHODS FOR REPAIRING BONE FRACTURES

(71) Applicant: Syntorr, Inc., Palo Alto, CA (US)

(72) Inventors: Daniel L. Martin, Palo Alto, CA (US); Jeremi M. Leasure, San Francisco, CA (US)

(73) Assignee: SIMFIX SURGICAL INC., Palo Alto, CA (US)

( * ) Notice: Subject to any disclaimer, the term of this patent is extended or adjusted under 35 U.S.C. 154(b) by 0 days.

(21) Appl. No.: 15/891,346

(22) Filed: Feb. 7, 2018

(65) Prior Publication Data
US 2018/0271573 A1 Sep. 27, 2018

Related U.S. Application Data

(60) Provisional application No. 62/455,953, filed on Feb. 7, 2017.

(51) Int. Cl.
*A61B 17/72* (2006.01)
*A61B 17/86* (2006.01)
*A61B 17/88* (2006.01)

(52) U.S. Cl.
CPC ...... *A61B 17/8635* (2013.01); *A61B 17/7208* (2013.01); *A61B 17/7233* (2013.01); *A61B 17/863* (2013.01); *A61B 17/866* (2013.01); *A61B 17/8861* (2013.01); *A61B 17/8863* (2013.01)

(58) Field of Classification Search
CPC . A61B 17/72; A61B 17/7208; A61B 17/7233; A61B 17/7283; A61B 17/84; A61B 17/842; A61B 17/846–17/848; A61B 17/8625–8635
See application file for complete search history.

(56) References Cited

U.S. PATENT DOCUMENTS

| | | | | |
|---|---|---|---|---|
| 2002/0198527 A1* | 12/2002 | Muckter | ............. | A61B 17/866 606/316 |
| 2005/0027294 A1* | 2/2005 | Woll | ................. | A61B 17/7291 606/62 |
| 2006/0195099 A1* | 8/2006 | Bottlang | ............. | A61B 17/863 606/67 |
| 2008/0243191 A1* | 10/2008 | Tipirneni | ............. | A61B 17/742 606/280 |
| 2008/0292429 A1* | 11/2008 | Hasenbohler | ...... | A61B 17/8625 411/413 |
| 2009/0048606 A1* | 2/2009 | Tipirneni | ........... | A61B 17/1735 606/104 |

(Continued)

*Primary Examiner* — Eduardo C Robert
*Assistant Examiner* — Michelle C Eckman
(74) *Attorney, Agent, or Firm* — Kim & Stewart LLP

(57) ABSTRACT

Devices and methods for repairing bone fractures are described herein. A pin directing device for steering a flexible bone screw is disclosed. A fluted entry tool for penetrating into cancellous bone without penetrating the far cortex of the bone is disclosed. A flexible bone screw having a rotational position marker positioned thereon at a terminal twenty-five percent of the shaft is disclosed. A flexible bone screw comprising at least eighty percent cold work hardened alloy is disclosed. A pin bending clamp having a transverse hole in the jaws is disclosed. A flexible bone screw with a cortex climbing thread portion at the tip, which is helicoid, is also disclosed.

14 Claims, 16 Drawing Sheets

(56) References Cited

U.S. PATENT DOCUMENTS

| | | | |
|---|---|---|---|
| 2009/0062868 A1* | 3/2009 | Casutt | A61B 17/7001 606/316 |
| 2009/0131936 A1* | 5/2009 | Tipirneni | A61B 17/683 606/64 |
| 2009/0131991 A1* | 5/2009 | Tipirneni | A61B 17/683 606/301 |
| 2009/0149890 A1* | 6/2009 | Martin | A61B 17/1717 606/316 |
| 2009/0210016 A1* | 8/2009 | Champagne | A61B 17/863 606/309 |
| 2009/0306718 A1* | 12/2009 | Tipirneni | A61B 17/683 606/263 |
| 2010/0268285 A1* | 10/2010 | Tipirneni | A61B 17/742 606/309 |
| 2010/0312292 A1* | 12/2010 | Tipirneni | A61B 17/683 606/86 R |
| 2011/0034925 A1* | 2/2011 | Tipirneni | A61B 17/683 606/62 |
| 2014/0114312 A1* | 4/2014 | Krause | A61B 17/8605 606/62 |
| 2016/0310187 A1* | 10/2016 | Leibinger | A61B 17/7032 |

\* cited by examiner

DEVICES AND METHODS FOR REPAIRING BONE FRACTURES

CROSS-REFERENCE TO RELATED APPLICATION(S)

This application claims the benefit of U.S. Provisional Patent Application Ser. No. 62/455,953, filed Feb. 7, 2017, which is incorporated by reference herein.

BACKGROUND

Field

The present disclosure generally relates to devices and methods for repairing bone fractures, and more specifically to improved flexible bone screw devices and methods.

Description of the Related Art

Surgical techniques for the treatment of bone fractures commonly known and used in the art include external fixation, pinning, and joint replacement. In some situations, each of these techniques can be inadequate for facilitating satisfactory recover of the bone fracture. A proximal humerus fracture, i.e., a fracture of the humerus near the humeral head, is one such case. Replacement of the shoulder joint with a prosthesis is a complex and invasive procedure that can lead to the death of elderly patients, for whom proximal humerus fractures are common. Similarly, internal fixation of a proximal humerus fracture with one or more humeral plates and bone screws may successfully maintain the correct position of the humerus fragments, but the extensive dissection of soft tissue that is an integral part of this approach leads to high morbidity.

In light of the above, flexible bone screws have been developed for treatment of certain fractures, such as the percutaneous fixation of softer bone tissue to stronger bone tissue. For example, in a proximal humerus fracture, one or more flexible bone screws can be employed to fix the cancellous bone of the humeral head to the cortical bone of the humerus bone shaft. Specifically, a flexible bone screw is introduced into the intramedullary cavity of a humerus through an opening in the antero-lateral cortex on a first side of the humerus. The flexible bone screw is then advanced, via rotation, into the intramedullary cavity along an interior surface of the cortex on a second side of the humerus, and threaded into the subchondral bone of the humeral head.

When initially advanced into the intramedullary cavity, threads at the tip of the flexible bone screw typically contact an interior surface of the cortex at some angle of incidence. Rotation of the flexible bone screw and contact between the threads and the interior surface of the cortex then cause the bone screw to move along the interior surface of the cortex toward the humeral head. Thus, during installation, the flexible bone screw undergoes significant bending while being rotated, similar to that experienced by a material sample undergoing a rotating beam test. As a result, the bone screw can subject to significant fatigue during a normal installation procedure, and plastically deform, heat, or even fail during the installation, each of which is highly undesirable.

Accordingly, there is a need in the art for a flexible bone screw capable of bending during rotation.

SUMMARY

Devices and methods for repairing bone fractures are described herein. A pin directing device for steering a flexible bone screw is disclosed. A fluted entry tool for penetrating into cancellous bone without penetrating the far cortex of the bone is disclosed. A flexible bone screw having a rotational position marker positioned thereon at a terminal twenty-five percent of the shaft is disclosed. A flexible bone screw comprising at least eighty percent cold work hardened alloy is disclosed. A pin bending clamp having a transverse hole in the jaws is disclosed. A flexible bone screw with a cortex climbing thread portion at the tip, which is helicoid, is also disclosed.

BRIEF DESCRIPTION OF THE DRAWINGS

So that the manner in which the above recited features of the present disclosure can be understood in detail, a more particular description of the disclosure, briefly summarized above, may be had by reference to examples, some of which are illustrated in the appended drawings. It is to be noted, however, that the appended drawings illustrate only exemplary examples and are therefore not to be considered limiting of its scope, may admit to other equally effective implementations.

Figure 1:
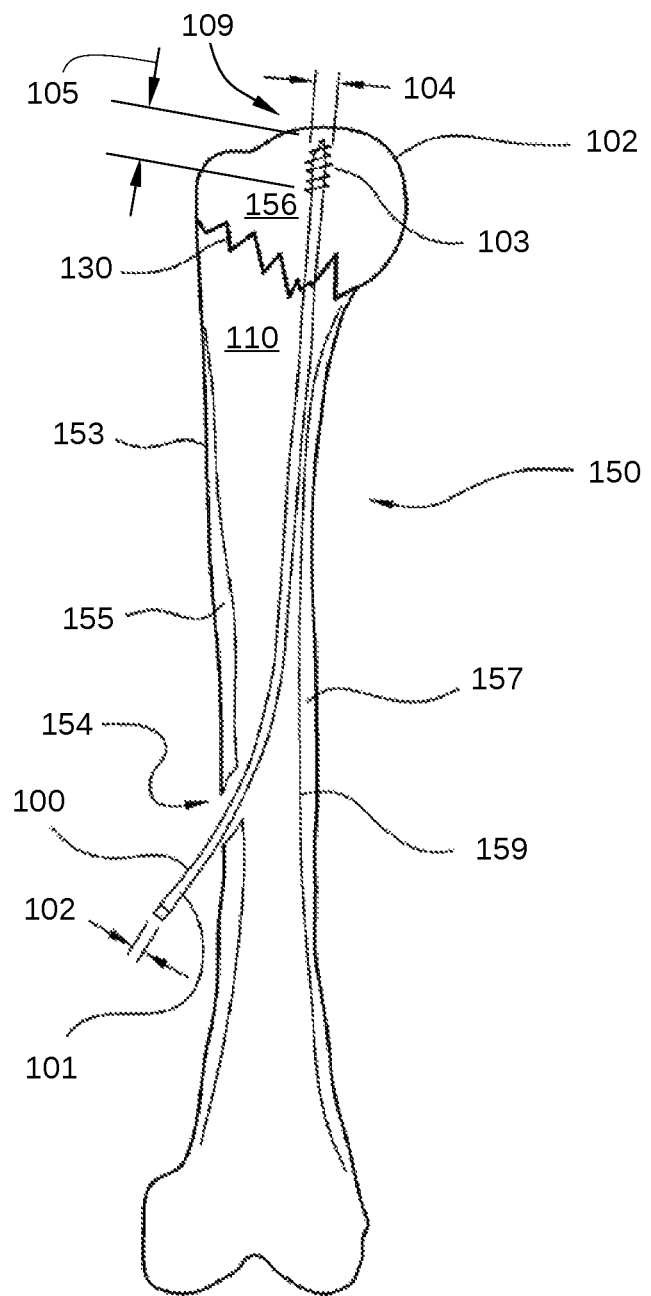
FIG. 1 illustrates the installation of a flexible bone screw for percutaneous fixation of a proximal humerus fracture, according to various embodiments of the disclosure.

To facilitate understanding, identical reference numerals have been used, where possible, to designate identical elements that are common to the figures. It is contemplated that elements and features of one implementation may be beneficially incorporated in other implementations without further recitation.

DETAILED DESCRIPTION

Flexible Bone Screw with Cold Worked Alloy

Cortical bone screws, which are designed for fixation of cortical bone, typically have a rounded tip, often a surface of revolution, that will not penetrate into cortical bone without a pilot hole, and will start to penetrate into cancellous bone only with considerable forward force. Cancellous bone screws, which are designed for fixation of cancellous bone, may have a reduced core diameter of the thread near a tapered tip, to facilitate penetration of both cortical bone and cancellous bone, without drilling a pilot hole. Some have cutting flutes, to facilitate cutting of threads into the bone, especially when there has been a pilot hole drilled. Some have trocar points, which are highly inclined to penetrate directly into cortical bone or cancellous bone, and not walk along the surface of the bone. Generally, the prior art screws have a geometry that is designed either to penetrate without a pilot hole, or to penetrate only with a pilot hole.

In the use of the flexible bone screw, penetration of the far cortex is not wanted. Rather, it is preferable to have the screw walk its way up the inside of the far cortex, without penetrating the far cortex, as illustrated in FIG. 1. FIG. 1 illustrates the installation of a flexible bone screw 100 for percutaneous fixation of a proximal humerus fracture 130, according to various embodiments of the disclosure. Specifically, flexible bone screw 100 fixes humeral head 152 of a humerus 100 to a bone shaft 153. First, humeral head 152 is returned to its proper position on bone shaft 153, using methods standard to the art of orthopedic surgery. Then, one or more flexible bone screws 100 are introduced into the intramedullary cavity 110 of humerus 150 through an entry hole 154 in the side cortex 155 of humerus 100. For clarity, only one flexible bone screw 100 is depicted in FIG. 1. Each flexible bone screw 100 is then advanced into the intramedullary cavity 110, along an inner surface 159 of a far cortex 157, and threaded into cancellous bone 156 of humerus 150. Thus, the flexible bone screw converts to an axial intramedullary device, with a tip 109 advanced across proximal humerus fracture 130, and further advanced into cancellous bone 156 in humeral head 152 without a pilot hole being formed.

As shown, during and after the installation process, there is significant bending of flexible bone screw 100. Thus, flexible bone screw 100 should be configured to allow elastic bending to a relatively small radius of curvature before plastic bending occurs. In addition, there is a need for a thread on tip 109 of flexible bone screw 100 that will climb along the inner surface of far cortex 107 during installation, rather than penetrate into cortical bone. Further, tip 109 should be configured to penetrate directly into a cancellous bone volume in response to being rotated during installation. Direct penetration into cancellous bone is especially desired when flexible bone screw 100 is engaging the cancellous bone while tip 109 is moving substantially along the axis of flexible bone screw 100 and tip 109.

According to various embodiments, an orthopedic screw device with cortex climbing thread, such as flexible bone screw 100, enables a tip to perform both functions. Flexible bone screw 100 is fabricated from stainless steel and includes a shaft 101 with a shaft diameter 102 and a threaded portion 103 located at tip 109. The surface of shaft 101 is substantially smooth, having a surface roughness, Ra, of less than about 3 micrometers, where the surface roughness is measured parallel to the axis of shaft 101. The smooth shaft surface allows easy gliding of shaft 101 into entry hole 154, so that if humeral head 152 should collapse, shaft 101 slides out of entry hole 154 rather than being engaged therewith, which would force threaded portion 103 through cancellous bone 156. Threaded portion 103 is positioned at one end of shaft 101 for engagement with bone material, has a length 105 and has an outer diameter 104 that is larger than shaft diameter 102. A tool engagement portion is positioned at the opposite end of shaft 101 to facilitate attachment of flexible bone screw 100 to a manual or powered screw-rotating device, and does not engage against bone. One example of such a tool engagement portion is tool engagement portion 1228, shown in FIG. 12. Flexible bone screw 100 is configured so that tool engagement portion 107 and any extra length of shaft 101 can be cut off at the completion of surgery. In this embodiment, shaft diameter 102 is between 1.7 mm and 3 mm; the overall length of flexible bone screw 100 is at least about 200 mm, preferably 300 mm; length 105 is between 6 mm and 25 mm, and outer diameter 104 is between 3 mm and 5 mm. Having a shaft diameter less than about 3 mm allows a shaft stiffness which is not excessive for manipulation by the surgeon during surgery. In order for flexible bone screw 100 to have sufficient flexibility for many applications, i.e., an elastic bending arc of at least 15°, in some embodiments, the ratio of the length of shaft 101 to shaft diameter 102 is at least about 50:1. In some embodiments, flexible bone screw 100 has an elastic bending arc that is at least about 30° and the ratio of the length of shaft 101 to shaft diameter 102 is at least about 100:1. Such an elastic bending arc avoids use of flexible bone screw being employed in the plastic deformation range, thereby preventing possible mechanical failure of flexible bone screw 100 during installation. The elastic bending arc of flexible bone screw 100 is described below in conjunction with FIG. 3.

In other embodiments, one or more features of flexible bone screw 100, as described above, may have different dimensions based on what bone is being treated, the location of the fracture, and other factors. For example, the ratio of length 105 to the overall length of shaft 101 may be as high as 0.20, the ratio of outer diameter 104 to shaft diameter 102 may vary between about 1.2 and about 4.0, and the possible elastic bending arc may be greater than 20° to 30°. Other features that may have different values include shaft diameter 102, outer diameter 104, length 105, and the overall length of shaft 101. Flexible bone screw 100 permits a large amount of strain prior to plastic deformation. Stated differently, shaft 101 allows elastic bending to a relatively small radius of curvature before plastic bending occurs. According to various embodiments described herein, while flexible bone screw 100 is spinning in a bent configuration, there is minimal or no plastic deformation of shaft 101. Plastic deformation in this situation is analogous to a rotating beam fatigue test, and may contribute to failure of flexible bone screw 100 through breakage. It is noted that flexible bone screw prototypes that were manufactured with standard stainless steel showed plastic deformation during the course of normal insertion as well as associated heating of the shaft during insertion. In some embodiments, such plastic deformation is prevented in flexible bone screw 100 by forming shaft 101 with a cold-worked alloy, i.e., with a material that has been strain hardened, as described below, or by choosing alloys that have a higher yield strain than standard stainless steel.

The motivation for choosing a cold worked alloy for flexible bone screw 100 is different than in conventional bone pins and screws. Specifically, flexible bone screw 100 is bent into an arc during spinning insertion, whereas other pins and screws generally have bending elastic strain requirement only after insertion. Conventional bone screws and pins are inserted strictly along a straight line, and do not require a high yield strain to prevent plastic deformation during insertion. Flexible bone screw 100 benefits from the high yield strain offered by cold working during the insertion process, which is different from other surgical screws and pins. That is, the high yield strain of the cold-worked material of shaft 101 protects shaft 101 from fatigue damage and failure during insertion. Manufacturing with cold-worked stainless steel alloy is more expensive than with a non cold worked (i.e., annealed) alloy, but the value offered by cold working is an unexpected added feature that justifies the added expense of manufacture.

The elastic bending tolerance of shaft 101 of flexible bone screw 100 may be approximated by the analytic consideration of Youngs modulus E, yield strength and dimensions of shaft 101, where yield strength (or yield stress) is the stress at which a material begins to deform plastically. During the spinning insertion of shaft 101 along an arcuate path, as shown in FIG. 1, there is a risk of continuous plastic deformation of shaft 101, such that there is reduced strength, and possible breakage. Such plastic deformation and associated breakage can be avoided by having the material of shaft 101 remain within the yield strain (elastic deformation regime) of the material while shaft 101 is bent during insertion. According to various embodiments, shaft 101 is formed from a material with higher yield strength than the conventional annealed stainless steel that is commonly employed in orthopedic devices. Increasing the yield strength of the material of shaft 101 directly increases the strain to yield of shaft 101, i.e., the amount of deflection that shaft 101 can undergo before beginning to plastically deform. When shaft 101 is formed of a material with higher strain to yield, the elastic bending arc of shaft 101 is increased, for example from 5° or less up to 30° or more. This increased elastic bending arc enables the radius of curvature of the bend during insertion to be shorter while shaft 101 remains within an elastic bending range. The elastic bending arc of a flexible bone screw is described below in conjunction with FIG. 2.

Figure 2:
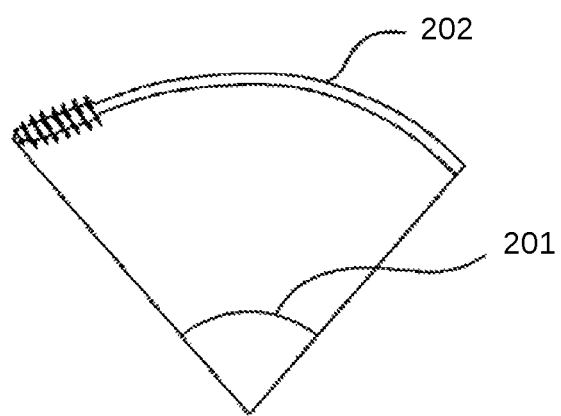
FIG. 2 illustrates the elastic bending arc of a flexible bone screw 202, where flexible bone screw 202 represents flexible bone screw 100 described in FIG. 1.

FIG. 2 illustrates the elastic bending arc 201 of a flexible bone screw 202, where flexible bone screw 202 represents flexible bone screw 100 described in FIG. 1. Elastic bending arc 201 is defined as the maximum arc of curvature, in degrees, that can be produced by flexible bone screw 202 without flexible bone screw 202 undergoing substantial plastic deformation. Hence, a more flexible bone screw has an elastic bending arc of greater degree than a less flexible bone screw. Elastic bending arc 201 defines how easily flexible bone screw 202 can be manipulated by the surgeon. Generally, the surgeon bends a flexible bone screw to a minimum arc of 15°, and preferably to an arc of 30°, without the use of excessive force or localized glove pressure, in order to insert the bone screw with hand held tools. For larger shaft diameters, the surgeon obtains greater bending leverage by having a correspondingly longer bone screw length, but elastic bending arc 201, in such a case, typically remains the same, and is preferably as large an angle as practicable.

The elastic bending arc of a flexible bone screw, according to various embodiments of the invention, is by design much greater than any other prior art bone screws formed from a metal or metal alloy that is not cold-worked. Such improved flexibility addresses specific previously unsolved needs in fracture treatment. This characteristic has been achieved by selecting a cold-worked alloy, i.e., a strain-hardened material, for forming a shaft of a flexible bone screw. It is noted that machining and other manufacturing processes are more difficult when performed on strain-hardened metal allow compared to an annealed metal alloy of the same composition. However, as set forth above, the increased flexibility of a flexible bone screw formed from a cold-worked metal alloy provides unique, novel advantages, as has been demonstrated by the inventor.

To achieve high yield strain for stainless steel, yield strain can be increased by nearly a factor of between five and ten, between the annealed state and fully cold worked state.

The Young's modulus of 316L is 193-200 GPa. In the non-cold-worked state, the yield strength is approximately 170 MPa. Fully cold worked yield strength is in the range of 1070-1600 MPa. The radius of curvature R achieved without plastic deformation is $$R = dE/2(\text{yield strength})$$

Where d is the shaft diameter. In an example, for a shaft diameter of 2 mm, the non-plastic deformation radius of curvature for non cold worked 316L: E=200 GPa, and yield strength =170 MPa, which gives a radius R of 1.18 m. By contrast, in an example of same shaft diameter of 2 mm, fully cold worked 316L, E=200 GPa, and yield strength =1600 MPa. This gives a radius R of 0.125 m. The forgoing comparison shows the dramatically increased safety achieved by using the cold worked material for shaft 101 of flexible bone screw 100.

316L stainless steel may be chosen in different grades of cold work tempers, as in ASTM A 666. Progressive increases in yield strength, and therefore reduction in elastic bending radius, are achieved with cold work, progressing from annealed, ¼ hard, ½ hard, ¾ hard, to full hard. The above examples represent the extremes from annealed to full hard. Similarly, Grade 5 Ti alloy and other mechanically similar Ti alloys, with a yield strength of 1100 MPa, also offer a high degree of safety with fatigue bending during spinning insertion, over non-cold worked 316L. Similarly, Grade 5 Ti alloy is more expensive in manufacture, compared to grades of commercially pure titanium. Therefore the choice of grade 5 Ti alloy may also be made to achieve the bending requirements found at insertion of the flexible bone screw.

There are no prior art bone screws that are designed to be threadedly advanced while bent into a 10° arc or greater. Thus, the flexible bone screw prevents a unique design challenge, requiring a combination of both dimensions and materials to render the device effective. More specifically, the special demands on the flexible bone screw shafts make the material requirements unique in combination with the dimensions and methodology of use. Smooth pins and bone screws made with non-cold-worked material are usable in other orthopedic applications, although they have lower yield strength. There are no other threaded orthopedic devices that are advanced while spinning and bent into a curve of 10° to 15° or more, as are flexible bone screws. The purpose for use of cold worked materials in other orthopedic implants is to achieve high yield strength, and they are generally designed to avoid having the intraosseous portion being bent into an arc while being advanced. Threaded orthopedic devices are generally designed to be stiff, rather than with dimensions and material properties to allow flexibility.

This disclosure specifies flexible bone screws having a length to shaft diameter ratio of greater than 50, and greater than 100, as well as a thread diameter to shaft diameter ratio of greater than 1.2, being fabricated from cold worked titanium or stainless steel alloys. In one example, the flexible bone screw 420 is made of a cold worked 300 series stainless steel, such as 316 stainless steel. In another example, the flexible bone screw 202 is made of a titanium alloy, especially grade 5 Titanium, or other mechanically equivalent Titanium alloy. In yet another example, the flexible bone screw 202 is made of an alloy that is hardened by an at least 49 percent cold work process. In one example, the cold work of the flexible bone screw 202 is greater than 80%. In another example, the cold work of the flexible bone screw 202 is greater than 90%. In some embodiments, the fabrication material of the disclosed flexible bone screw 202 with cold worked alloy may be "spring hard," the flexible bone screw 202 is flexible and may spring, but is not too hard for use in repairing bone fractures, when resiliency is desired to maintain the integrity of the flexible bone screw 202 that has been inserted into the patient.

The cold working is one of the only means to achieve the required hardness, or yield strength, in the stainless steel alloys and metals that are typically used for orthopedic implant applications. The combination of the design dimensions of the flexible bone screw 202 with the cold working of the metal provides advantages that cannot be accrued with adding cold working to the metal of other orthopedic implants having different dimensional features. The cold working allows the flexible bone screw 202 to be more effective in its role as a flexible device, whereas use of cold worked alloys does not allow other orthopedic devices to be used effectively as flexible bone screws. Cold worked materials can add to the unique attributes of the flexible bone screw 202, i.e., as a device that is elastically bent during insertion, compared to other orthopedic devices that are not designed to be substantially elastically bent during the normal course of insertion. Use of grade 5 titanium is another example of selection of an implant material with a high yield strain, making it in combination with the dimensions of the flexible bone screw, suitable for elastic bending during insertion.

In some embodiments, a flexible bone screw comprises an elongated shaft that is configured for elastic bending and a threaded portion at one end of the shaft for engagement with a bone. In such embodiments, the threaded portion has an outer diameter that is larger than a diameter of the shaft. In some embodiments, the flexible bone screw comprises at least eighty percent cold worked hardening alloy. In some embodiments, the flexible bone screw comprises an alloy that is hardened by an at least 49 percent cold work process. In some embodiments, the flexible bone screw comprises grade 5 titanium.

Orthopedic Screw Device with Cortex Climbing Thread

Figure 3B:
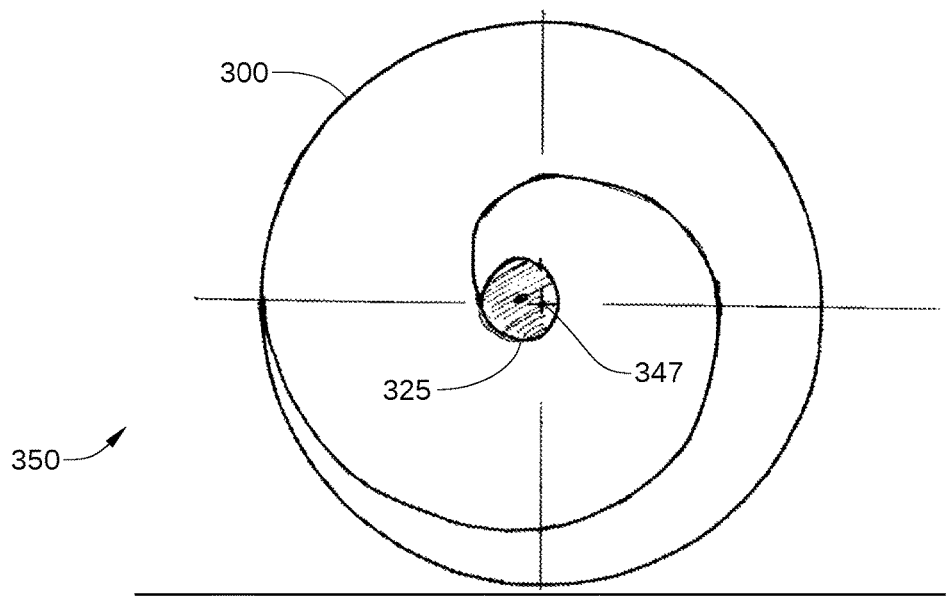
FIG. 3B is an end-view projection of the orthopedic screw device of FIG. 3A, according to an embodiment of the present disclosure.
Figure 3A:
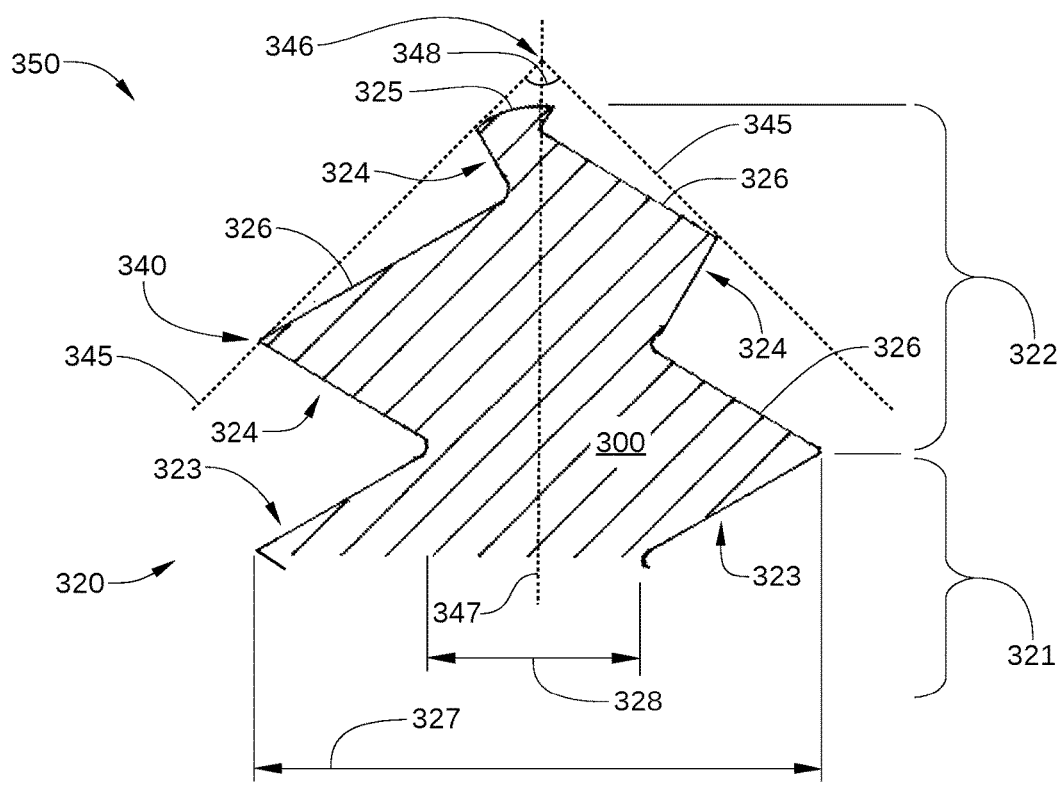
FIG. 3A is cross-sectional view of an orthopedic screw device, according to the present disclosure.

FIG. 3A is cross-sectional view of an orthopedic screw device 300, such as a flexible bone screw with a cortex climbing thread 250, according to the present disclosure. FIG. 3B is an end-view projection of the orthopedic screw device 300 of FIG. 3A.

The tip of the orthopedic screw device 300 is designed with a cortex climbing thread 350, which is configured to penetrate cancellous bone without a pilot hole and to avoid penetration into cortical bone. Cortex climbing thread 350 is part of a threaded portion 320 of orthopedic screw device 300. The special application for cortex climbing thread 350 is in a flexible bone screw, where the screw is inserted obliquely through a hole in the side of the bony cortex, and the screw encounters the far cortex at an acute angle. Usually this angle is less than about 45°. For example, threaded portion 320 can be employed as threaded portion 103 of flexible bone screw 100 in FIG. 1.

The cortex climbing thread 350 is an orthopedic bone screw thread that is at a tip of the orthopedic screw device 300, and includes a body region 321 and a tip region 322. Body region 321 includes a body thread 323 and tip region 322 includes a tip thread 324 and a tip 325. Tip thread 324 includes helicoid surfaces 326. In some embodiments, tip 325 is rounded. Generally body thread 323 has a cylindrical profile, but sometimes body thread 323 has a gentle taper or other diametric variation, such as less than 5° angulation of opposing sidewalls of the body thread. By contrast, tip thread 324 is configured as a helicoid with a decreasing (or tapering) radius. This disclosure describes a cortex climbing thread 350 that is between tip 325 of orthopedic screw device 300 and is within a distance of approximately two diameters proximal to tip 325 of orthopedic screw device 300.

The spatial domain of the cortex climbing thread 350 is between tip 325 and a transition point 340 where body thread 323 joins or becomes tip thread 324, i.e., where the outer diameter (thread major diameter of tip thread 324 equals a thread major diameter 327 of body thread 323. It is noted that the thread major diameter of tip thread 324 decreases to tip 325 and is less than thread major diameter 327 except at transition point 340. The spatial domain of cortex climbing thread 350 may be described according to a cone 345 (shown as dashed lines in FIG. 3A) in space proximate the tip of threaded orthopedic screw device 300. Cone 345 is oriented such that an apex 346 of cone 345 is generally near tip 325, is centered about an axis 347 of threaded orthopedic screw device 300, and intersects transition point 340. Often there is also a small rounding of the very tip of the screw, to prevent undesired occurrences, such as ripping of the surgeons gloves. In some embodiments, a typical aperture angle 348 of cone 345 is 90°. In addition, the base of cone 345 is coincident with the circle where the cylinder of the thread body is intersected, i.e., a circle perpendicular to axis 347 and including transition point 340. Tip thread 324 is included entirely within cone 345. The cortex climbing thread 350 may contact the surface of cone 345, but does not extend beyond the surface of cone 345. The cone containing the physical domain of cortex climbing thread 350 can be with an aperture angle 348 of as low as 45° at the tip or as high as 120° at the tip. By restricting the physical domain of cortex climbing thread 350 to remaining within cone 345 as described herein, cortex climbing thread 350 is prevented from penetrating far cortex 157 (shown in FIG. 1) when contacting far cortex 157 at an oblique angle, and is much more likely to advance along far cortex 157 during installation, as desired. The cone containing the thread may also be defined by contact with thread crests near the axis 347, and a distance away from the axis, for example the thread crest that is halfway between the axis 347 and the diameter 327. Such a thread will also contact a cortical wall before the tip, when impinging at an angle less than ½ the angle of the cone. As such it will also serve as a climbing thread.

As shown in FIG. 3B, when viewing the end of orthopedic screw device 300 from the tip end, the surface of the tip that is seen may be a surface having a form that is a helicoid. The helicoid surface seen does not form part of a cone or other surface of revolution about the screw axis (i.e., about axis 347). A vector line from axis 347 of the screw and partially lying in the surface of the helicoid may make an angle with the axis that is different from 90°. The converging spiral of the crest of the cortex climbing thread 350 may contact a surface of a cone, but there is not a substantial surface area of the thread (when viewed on an end-view along axis 347) that is coincident with a conical surface or other surface of revolution. Stated another way, less than 20% of the surface seen in an end view (a projected surface) coincides with a conical or other surface of revolution. Stated another way, the end view does not reveal a thread surface that is cut onto the surface of a cone or other surface of revolution, with residual surface of revolution. Stated another way, the end view does not reveal a thread that is part of the surface of a cone or other surface of revolution, leaving residual cone or surface of revolution in more than 20%, or 10%, of the area of the end-on view. Stated another way, the surface area in FIG. 4 (described below) that represents a surface of revolution, is less than 20%, or 10%, of the surface area shown in the end-on view in FIG. 3B.

To enable cortex climbing thread 350 to positively engage with and advance into the intended bone material, such as cancellous bone 156 in FIG. 1, no more than a small portion of helicoid surfaces 326 are coincident with a surface of rotation that is centered on axis 347. One such embodiment is described below in conjunction with FIG. 4.

Figure 4:
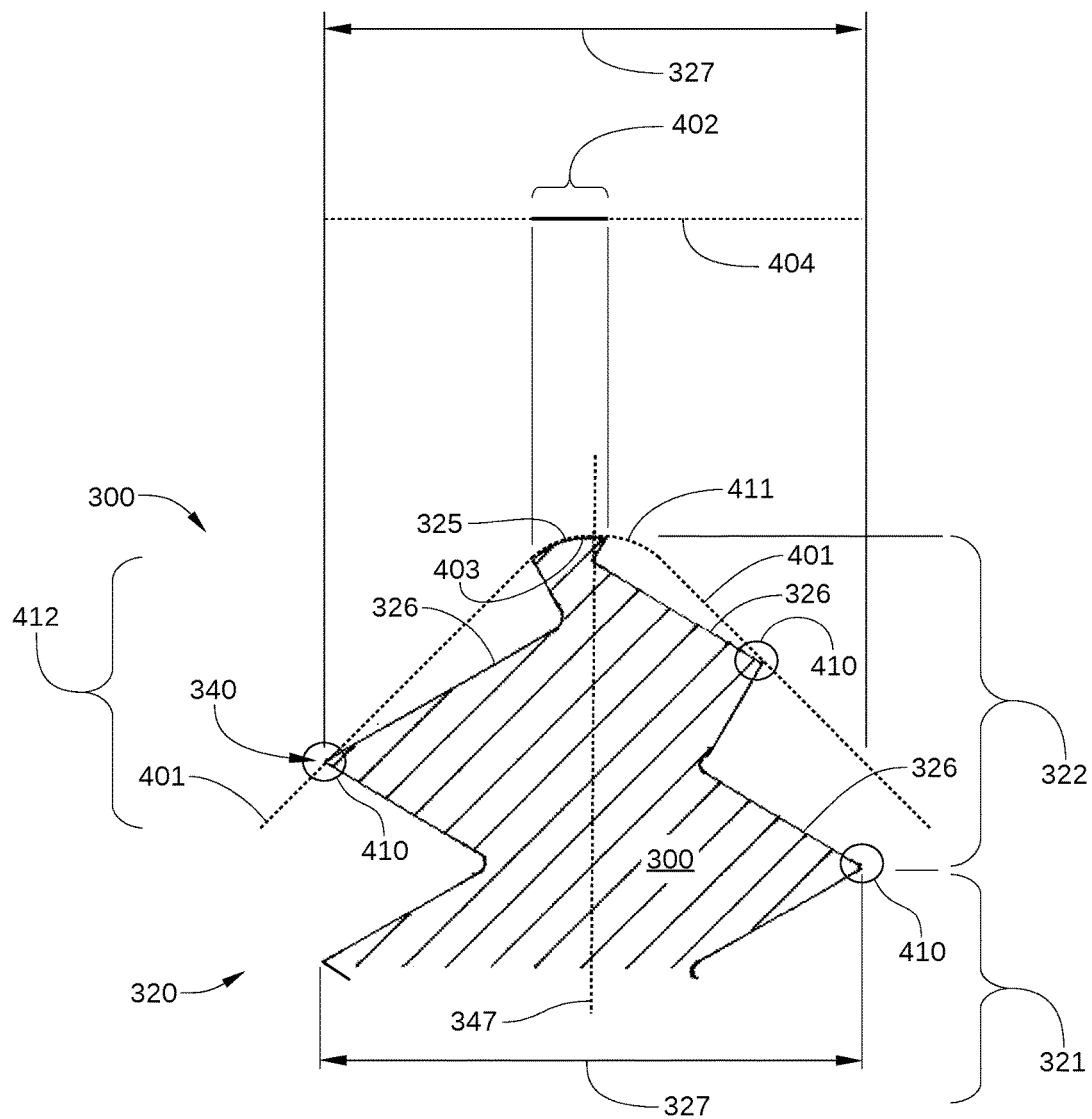
FIG. 4 is cross-sectional view of the orthopedic screw device of FIGS. 3A and 3B, a surface of rotation, and a projected surface area of helicoid surfaces that are coincident with the surface of rotation, according to an embodiment of the present disclosure.

FIG. 4 is cross-sectional view of orthopedic screw device 300, a surface of rotation 401, and a projected surface area 402 of helicoid surfaces 326 that are coincident with surface of rotation 401, according to an embodiment of the present disclosure. As shown, surface of rotation 401, shown in profile in FIG. 4, is centered about axis 347. Surface of rotation 401 can be defined by the rotation about axis 347 of any curve segment that includes transition point 340 and intersects axis 347, and can have any continuous cross-sectional profile. For purposes of illustration, in the embodiment illustrated in FIG. 4, surface of rotation 401 is configured to coincide with, as closely as possible, helicoid surfaces 326. Thus, in FIG. 4, surface of rotation 401 includes a curved portion 411 that is proximate tip 325 and a straight-walled, cone-like portion 412 that includes transition point 340. In other embodiments, surface of rotation 401 can include any arbitrary shape that is rotated about axis 347. It is noted that, because helicoid surfaces 326 have a decreasing radius that tapers towards tip 325, cone-like portion 412 does not coincide with a significant portion of helicoid surface 326.

Projected surface area 402 indicates a projected area of helicoid surfaces 326 that are coincident with surface of rotation 401. Projected surface area 402 is the projected area (when viewed along axis 347) that is coincident with any portion of any possible surface of rotation for example surface of rotation 401 or tip 325. In the embodiment illustrated in FIG. 4, the somewhat spherical surface 403 of tip 325 is itself a surface of revolution, and therefore is coincident with curved portion 411 of surface of rotation 401. However, helicoid surfaces 326 only intersect with surface of rotation 401 along a curve, and therefore are not coincident with surface of rotation 401 over a significant area. As shown, projected surface area 402 is less than 20% of the total projected area 404 of helicoid surfaces 326, where total projected area 404 is the area of a circle with a diameter corresponding to thread major diameter 327. As a result, when orthopedic screw device 300 contacts bone material (such as cancellous bone 156) with cortex climbing thread 350, orthopedic screw device 300 will not simply spin in place. Instead, cortex climbing thread 350 will positively engage the bony material and advance into the bony material without the need for high axial force.

The pitch and phase of the cortex climbing thread 350 may be substantially the same as or different from the pitch of the body thread of the orthopedic device. In some embodiments, the cortex climbing thread 350 may have a double lead thread within the spatial domain of the cone, each of the leads may have the same pitch.

The purpose of avoiding surface of revolution at the tip is that the surface of revolution will tend to spin against cancellous bone and not penetrate. With surface of revolution surface geometry, as a crest 410 of the cortex climbing thread 350 spins against the bone, there is no relief angle immediately behind the leading crest 410 of the cortex climbing thread 350. If, on the other hand, the tip surface facing the bone is a helicoid, then crest 410 of the cortex climbing thread 350 has a relief behind the crest 410 that allows the cortex climbing thread 350 to draw directly into bone. For purposes of illustration, a threaded portion of a screw tip that has significant tip surfaces that do coincide with a surface of rotation will now be described.

Figure 5:
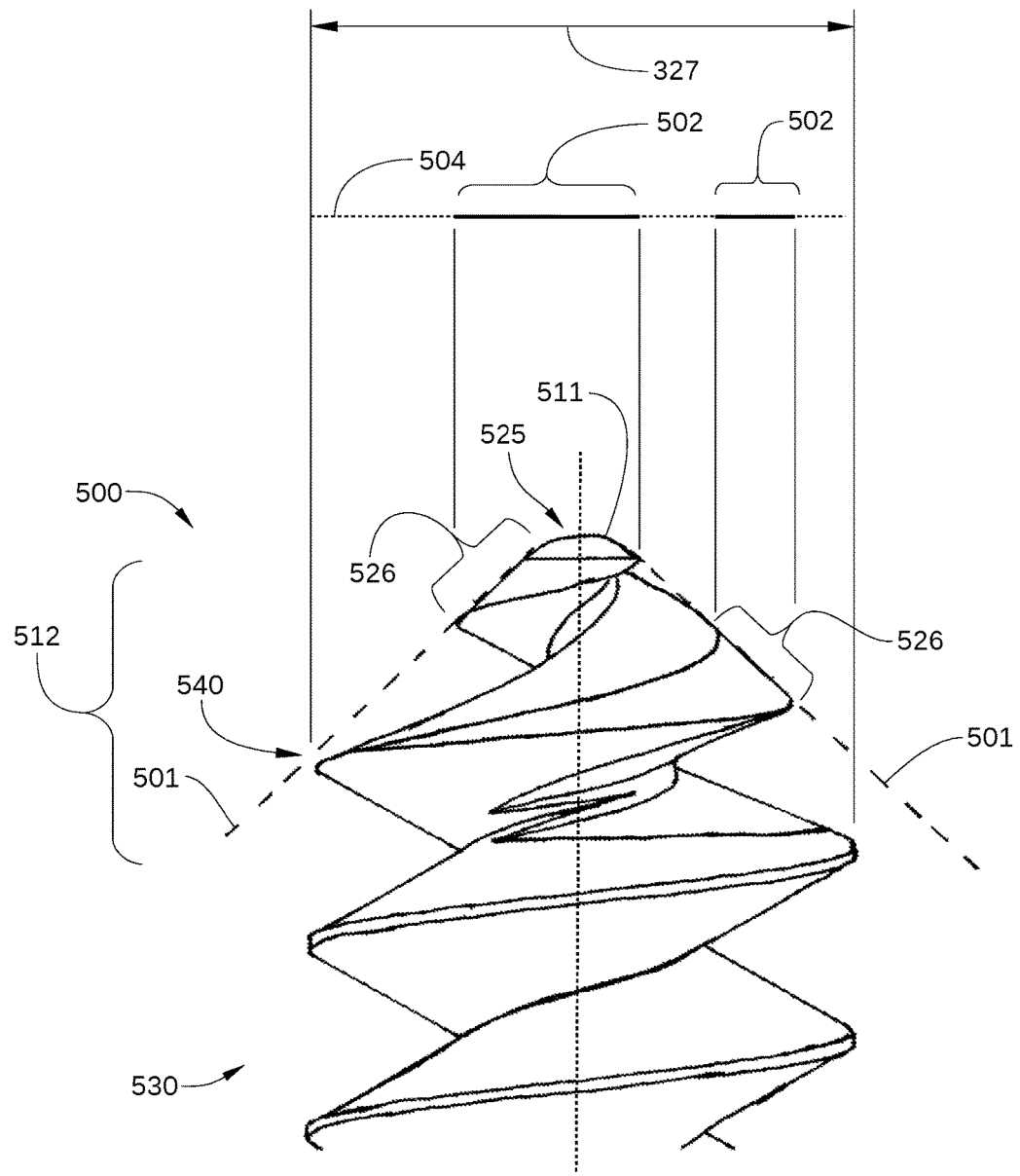
FIG. 5 is a side view of a screw tip that includes a significant surface area that is coincident with a surface of rotation, according to an embodiment of the present disclosure.

FIG. 5 is a side view of a screw tip 500 that includes a significant surface area that is coincident with a surface of rotation 501, according to an embodiment of the present disclosure. FIG. 5 further includes a projected surface area 502 of surfaces 526 that are coincident with surface of rotation 501. Surface of revolution 501 includes a curved portion 511 that is coincident with a rounded tip 525 of screw tip 500 and a cone-like portion 512 that is coincident with multiple surfaces 526 of a thread 530. As shown, a projected surface area 502 is more than 20% of the total projected area 504 multiple surfaces 526. The high projected surface area 502 that is coincident with surface of rotation 501 indicates that contact with a bony material by screw tip 500 while screw tip 500 is rotating can result in screw tip 500 spinning in place against the bony material, rather than actively engaging and entering the bony material.

Thus, the helicoid surface geometry of cortex climbing thread 350 (shown in FIG. 3A) enhances the lead, or entry, into cancellous bone. If, however, cone 345 is of a high aperture angle, for example 90°, the lead into hard cortical bone is inhibited. The geometry of the spiral helix of cortex climbing thread 350 may be viewed as a sort of spiral wedding cake or as a Tower of Babel as it is represented in illustrations. The walkway on the Tower of Babel is that facing toward the tip of the tower or the tip of the screw. That walkway is one form of a helicoid surface. The edges of the walkway may contact a conical surface or other converging surface of revolution, but the surface of the walkway or the surface of the helicoid is not part of the surface of the cone.

The aperture angle of the cone of the tip defines the incidence angle of orthopedic screw device 300 against the surface of cortical bone at which it tends to climb rather than penetrate. The aperture angle of the cone may be as great as 120°, or as little as 60°. For example, if the cone aperture angle of cone 345 is 90°, and orthopedic screw device 300 impinges against the inner sidewall of the far cortex at less than 45°, the base of the cone at the full diameter of body thread 323 will contact the sidewall of the cortex, before tip 325 contacts the sidewall of the cortex. Rotation of the orthopedic device will then cause the cortex climbing thread 350 to climb along the cortical wall toward the desired final location of orthopedic screw device 300. Yet, the helicoid geometry of the cortex climbing thread 350 of orthopedic screw device 300 will promote penetration into the cancellous bone at the other end of the canal when tip 325 arrives at that location.

The core diameter of cortex climbing thread 350 is reduced at locations within cone 345, relative to thread core diameter 328 of body thread 323 of orthopedic screw device 300. The core diameter of the cortex climbing thread 350 may approach zero near apex 346 of cone 345, i.e., near tip 325. The core diameter of the cortex climbing thread 350 may also be reduced in areas of the body thread that are adjacent to the cortex climbing thread 350.

The orthopedic screw device 300, such as a flexible bone screw with a cortex climbing thread 350, may also be described as follows. The thread at the tip is helicoid convergent on the tip of the screw, with the margin of the helicoid being tangent to, or touching, a surface of revolution. The surface of revolution has its widest dimension where its surface intersects the cylinder or other surface of revolution that is defining the outer diameter of the main thread body. The smallest transverse dimension (i.e., perpendicular to axis 347) of the surface of revolution is zero, at the tip of the screw. Thus, in some embodiments, between the intersection of the main thread body (body region 321) and the surface of revolution and the tip of the screw, the helicoid (tip region 322) is contained within or is tangent to a right circular cone (cone 345), having diameter 2r at the base, and height h from the base to the apex. The cone may also be defined according to the aperture angle, where the aperture angle is $2\theta$, where $\theta$ is the angle between the cone axis and the side of the cone. A portion of the helicoid forms a surface of tip thread 324 that is visualized in the end-on projection of the tip. Specifically, when viewed from the tip end, the surface visualized does not form more than 10% or 20% of a surface of revolution, and the surface viewed is primarily a helicoid surface. In some embodiments, the point of tip 325 is rounded, and in such embodiments, the rounded portion of tip 325 does form a surface of revolution with small surface area. The helicoid surface shown as 326, makes an angle with axis 347. This angle may be as high as 90°, or may be less than 90° but greater than 80°, or may be greater than 70°, or may be greater than 60°. Alternatively this angle may be greater than 50° and up to 60°.

In operation, a hole is made in the side of a bone during the course of orthopedic surgery. The hole maybe made oblique by tilting the entry tool drilling device. The orthopedic device with the cortex climbing thread 350 at the tip is inserted into the hole, to a depth where the shaft of the orthopedic device is resting in the hole. The shaft diameter is less than the hole diameter, and this will allow for added obliquity of the orthopedic device with respect to the axis of the bone. The orthopedic device is inserted at an angle such that it impinges against the opposite cortex at an angle which is less than one half of the cone aperture angle. In the case of the prior example, that would be an angle of less than 45°. The orthopedic device is spun and advanced. Mild forward pressure is applied. The thread at the base of the cone geometry touches the wall of cortex, and the cortex climbing thread 350 of the orthopedic device climbs up the wall. If the orthopedic device is the flexible bone screw, then climbing up the wall is associated with elastic bending of the shaft of the flexible bone screw, and as the flexible bone screw progresses up the intramedullary canal, it becomes an axial intramedullary device. As the tip of the orthopedic device encounters cancellous bone at the far end of the canal, there is no cortical wall to walk on, and it penetrates directly straight into the cancellous bone.

The tip of the orthopedic screw device 300 is designed with a cortex climbing thread 350, which can also penetrate cancellous bone without a pilot hole and yet avoids penetration into the far cortex of the cortical bone.

The thread at the tip combines uniquely with the helicoid thread geometry, that reduced surface area of rotation at the tip of the screw, and conical aperture of greater than 90°. The conical aperture angle enables the screw to climb the far cortex with an incidence angle of less than 45°, without cortical bone penetration, and the helicoid thread at the blunt tip allows the tip to penetrate straight into cancellous bone. The reduced surface area of a surface of rotation at the tip further facilitates entry into cancellous bone, so that the tip does not act as a drill. These features combine uniquely to make the flexible bone screw effective.

In some embodiments, a threaded orthopedic device comprises a flexible shaft and a threaded portion that is disposed on one end of the shaft. The threaded portion includes a tip region with a tip thread, a body portion with a body thread that has a major diameter that is equal to or greater than the largest major diameter of the tip thread, and a transition point disposed where an edge surface of the tip thread meets an edge surface of the body thread. The tip region is disposed within a cone that is 1) centered on a longitudinal axis of the shaft and 2) passes through the transition point. In some embodiments, a projected area of a portion of the surfaces of the tip thread that are coincident with a second surface of revolution, which is symmetrically positioned around a longitudinal axis of the shaft, is no more than 30% of the total projected area of the surfaces of the tip thread. In some embodiments, the projected area of the portion of the surfaces of the tip thread that are coincident with the second surface of revolution is no more than 10% of the total projected area of the surfaces of the tip thread. In some embodiments, the projected area of the portion of the surfaces of the tip thread that are coincident with the second surface of revolution is no more than 5% of the total projected area of the surfaces of the tip thread.

In some embodiments, the tip thread of the threaded orthopedic device is configured as a decreasing radius helicoid. In some embodiments, the tip thread is disposed within and does not extend beyond a cone having an aperture angle of 90° or greater and symmetrically positioned around a longitudinal axis of the shaft. In some embodiments, the cone contacts the tip thread where the tip thread meets the body thread. In some embodiments, the cone also contacts the tip thread closest to the tip of the tip thread, and the contact in these two locations defines the angle of the cone. In some embodiments, the cone is an example of a surface of revolution about the longitudinal axis of the shaft. In some embodiments, different surfaces of revolution than a cone can be employed to define the dimensional limits of the converging thread of the tip thread. For example, in such embodiments, the tip region could be defined (i.e., reside within) a sphere.

In some embodiments, the tip thread converges from the body thread of the screw so that a minimized area of the tip thread is coincident with any surface of revolution centered on the axis of the shaft and including the transition point. In such embodiments, a crest of the tip thread may touch the conical surface of revolution that defines the tip thread, with our sharing surface area. In some embodiments, the tip thread has a geometry that preserves a helicoid surface facing the tip end of the screw, and thereby avoids having substantial surface area that is coincident with any possible surface of revolution.

In some embodiments, the point of the screw is rounded to avoid excessive sharpness. In such embodiments, this rounded point may be a surface of revolution that is included in the sum fraction of the tip thread surface that is coincident with a surface of revolution. In some embodiments, the tip thread is defined as the thread that is between the screw point and the substantially constant diameter body thread. In some embodiments, the purpose of the helicoid geometry of the tip thread is to facilitate entry into cancellous bone in the axial direction. In some embodiments, multiple different thread profiles can be employed that provide a helicoid surface facing the tip end of the screw and avoiding surfaces of rotation.

In some embodiments, a flexible bone screw comprises a threaded tip configured for climbing the far cortex of bone, wherein as seen from the threaded tip end, the projected tip surface area is coincident with less than 30% a surface of revolution. In some embodiments, the projected tip surface of the flexible bone screw is at least 70% helicoid. In some embodiments, the projected tip surface of the flexible bone screw is at least 85% helicoid. In some embodiments, the projected tip surface of the flexible bone screw is at least 15% helicoid.

Fluted Entry Tool

Figure 6:
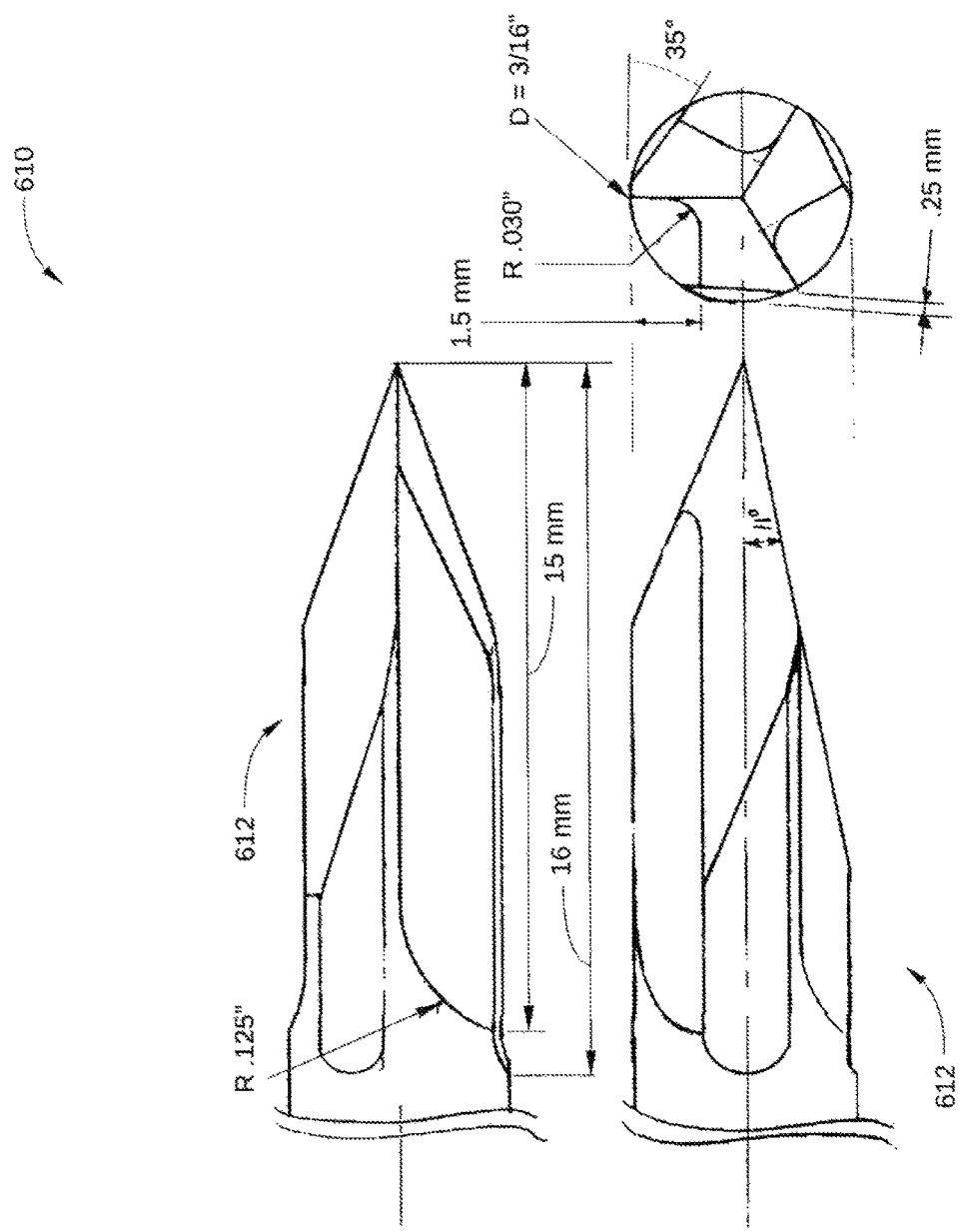
FIG. 6 depicts multiple views of a tip of a fluted entry tool according to embodiments of the present disclosure.

FIG. 6 depicts multiple views of a tip 612 of a fluted entry tool 610 according to the present disclosure.

The fluted entry tool 610 is generally used for making holes through a single cortex in bone from an exterior surface thereof. The fluted entry tool 610 is designed to avoid plunging through the bone and making a hole in the far side of the cortex. The fluted entry tool 610 is also designed to allow a moderate amount of side cutting when the shaft is tilted sideways in the hole. This is an important added capability compared to commonly used trocar points. It has a sharp point to prevent it from walking along the surface of a bone as the fluted entry tool 610 is rotated after initial contact with the exterior surface of the cortex, to initiate penetration of the bone at exactly the desired location, and also to prevent slipping off the side of the bone and injuring a neurovascular structure. The tip of this fluted entry tool 610 has a very short length of irregular side profile and flutes, e.g., less than about 2 cm, to prevent capturing and winding of soft tissues around the shaft as it is rotated. It is anticipated that in most cases this fluted entry tool 610 will not require the use of a tissue protector, saving additional required assistance in executing the surgical procedure.

The fluted entry tool 610 is generally a substantially cylindrical drilling tool, with drilling features at the very tip. The sides of the fluted entry tool 610, which are away from the tip, are smooth to prevent winding up soft tissues. This compares to the usual drill with spiral flutes, and flutes extending greater than 2.5 or 5 cm from the tip of the tool. The fluted entry tool 610 has features to allow drilling, typically a trocar point, with three facets located 120° apart, but it may also have greater than three facets, or another configuration that allows drilling. The facets trocar-type points have a plane angle relative to tool axis angle of typically less than 20°, and typically more than 8°. The facets converge to a sharp point. The facets may be surfaces that are planar as well as surfaces other than planar surfaces. There are generally one or more flutes beginning several millimeters (mm), for example 5 mm, from the tip, and extending to a position proximal to the facets, but less than 30 mm from the tip. There may be relief cuts or grooves that are ground on the side of the tool, adjacent to the flutes, to enhance the side-cutting action.

Figure 7:
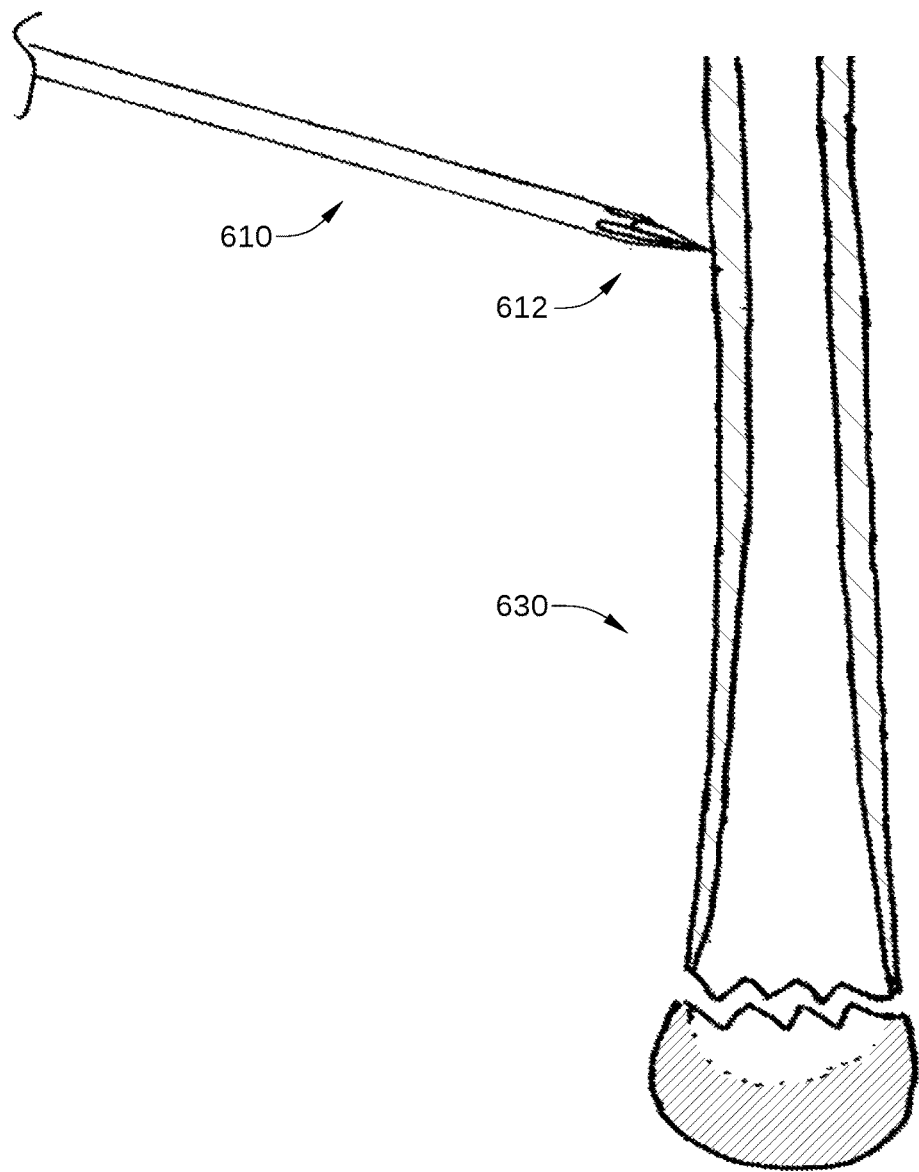
FIG. 7 is an illustration of a fluted entry tool tilted to initiate oblique entry into the bone in an approximately orthogonal direction to the surface of a bone, according to an embodiment of the present disclosure.
Figure 8:
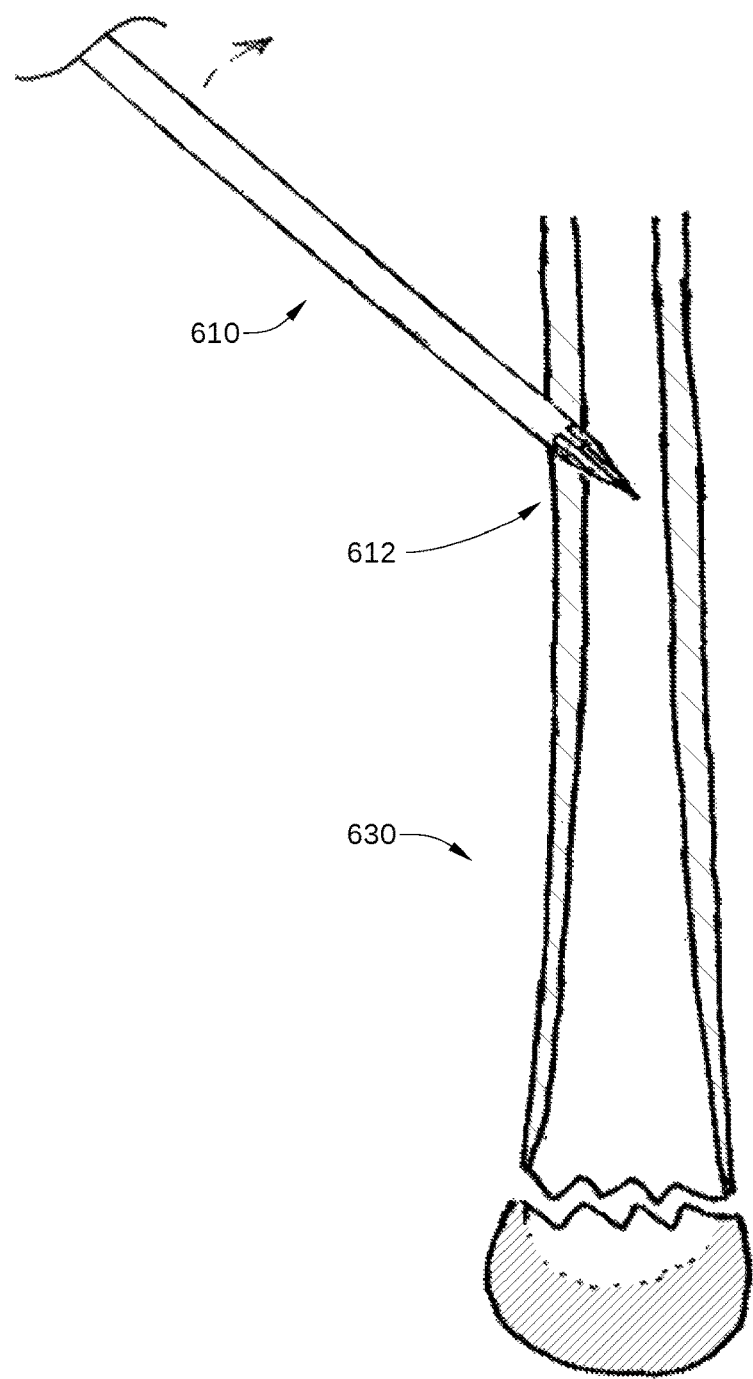
FIG. 8 is an illustration of the fluted entry tool of FIG. 7 tilted to initiate oblique entry into a bone, according to an embodiment of the present disclosure.

One example of a method of operation of the fluted entry tool 610 is as follows. A skin incision may be made, exposing the surface of a bone 630 to be penetrated. The fluted entry tool 610 is mounted onto a powered drilling apparatus (not shown). The tip of the fluted entry tool 610 is placed against the surface of bone 630 and spinning of the fluted entry tool 610 is initiated. Tip 612 does not walk along the surface of the bone and does not slip off to possibly cause injury to adjacent neurovascular structures. Further, pressure is applied to advance the fluted entry tool 610 in an approximately orthogonal direction to the surface of the bone, as shown in FIG. 7. As penetration into the bone is achieved, the fluted entry tool 610 is then tilted to initiate oblique entry into the bone, as shown in FIG. 8. As the surgeon notices penetration of the inside of the cortex, less forward force may be applied, and further tilting of the drill may be initiated. The fluted entry tool 610 is then advanced into the cortex to create an oblique hole. The diameter, or maximum transverse dimension, of the oblique hole may be larger than the diameter of the fluted entry tool 610. The fluted entry tool 610 may further include relief surfaces adjacent to the one or more flutes such that a distance from a surface to an axis is less than a distance from a margin of one of the one or more flutes to the axis.

One benefit of the fluted entry tool 610 is the trocar, which prevents or reduces walking along the surface of the bone. The trocar combined with flutes allows clearance of chip, or drilling debris, reducing the heating action of the tool as it drills past the midlength of the facet, and allows some full diameter cutting action that is normally not allowed by a trocar point. Additionally, the taper of the tip is at a relatively low angle, so the tip of the point passes through the inside wall of the cortex before the full diameter of the hole is made in the cortex. In this way, decreased required drilling force is noted by the surgeon, so that the surgeon knows that the cortex has been penetrated. The surgeon then reduces forward drilling force, such that the drilling tool does not plunge suddenly through the cortex. This prevents making an unwanted hole on the far side of the intramedullary canal, and allows a very controlled formation of the hole with controlled forward forced and tilting of the drill-tool unit. Additionally, tilting of the drill creates an oblique entry hole.

In some embodiments, a fluted entry tool comprises a trocar with three facets, each of the three facets being spaced 120 degrees apart; a trocar pointed tip at a point of convergence of the three facets, wherein the trocar pointed tip is configured to penetrate a surface of a bone; and one or more flutes beginning about 5 millimeters from the trocar pointed tip and extending to a position proximal to the three facets, but less than 30 millimeters from the tip. In some embodiments, a fluted entry tool comprises a trocar-type point having three or more facets, each of the three or more facets being spaced approximately an equal number of degrees apart; a trocar pointed tip at a point of convergence of the three or more facets, wherein the trocar pointed tip is configured to penetrate a surface of a bone; and one or more flutes beginning about 5 millimeters from the trocar pointed tip and extending to a position proximal to the three or more facets, but less than 30 millimeters from the tip. In some embodiments, the fluted entry tool further comprises relief surfaces adjacent to the one or more flutes, wherein a distance from a surface to an axis is less than a distance from a maximum radius margin of one of the one or more flutes to the axis. In some embodiments, the three or more facets are at an angle between 20 degrees and 8 degrees to the axis.

Pin Directing Device

Figure 9:
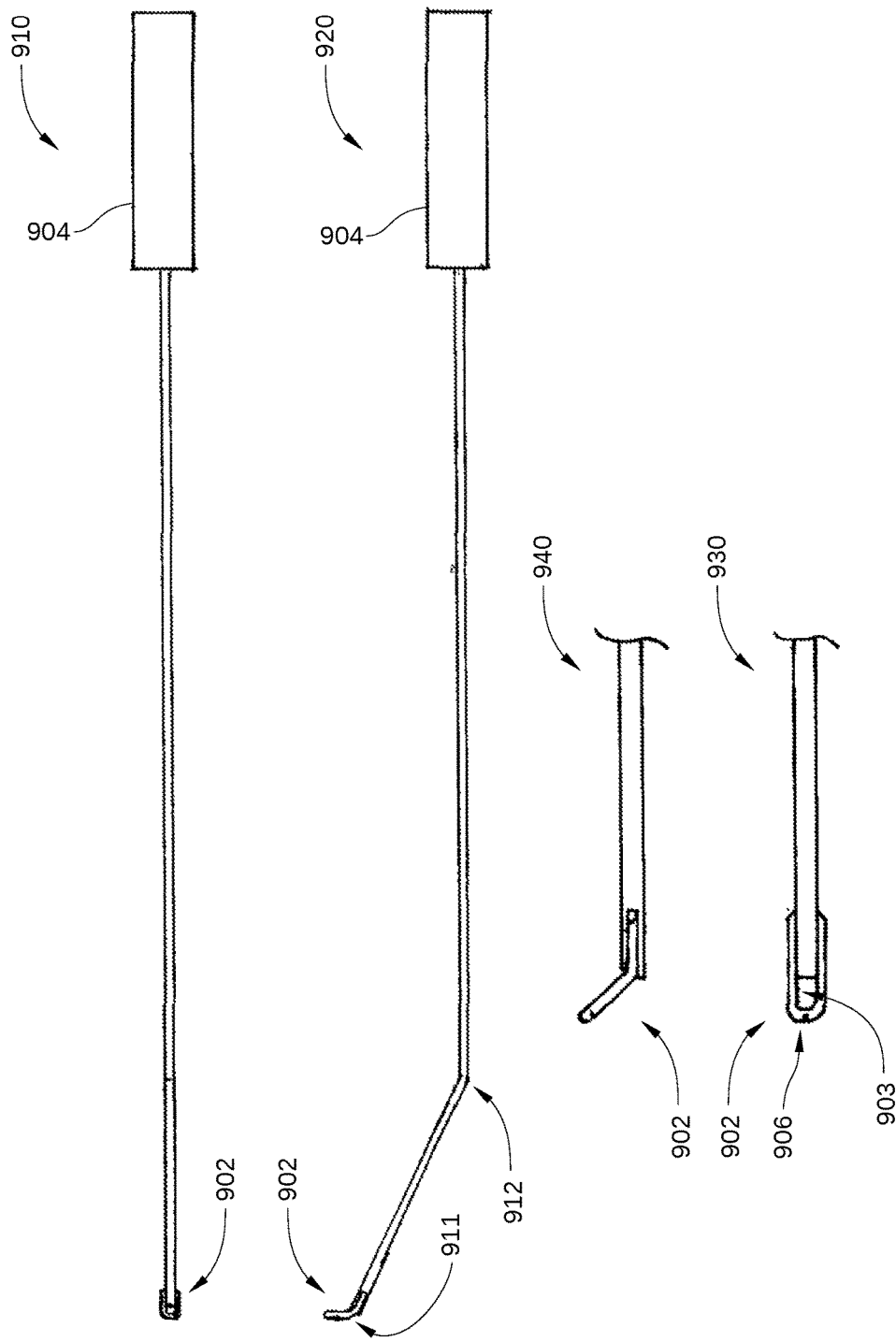
FIG. 9 includes multiple views of a pin directing device, according to embodiments of the present disclosure.

FIG. 9 includes multiple views of a pin directing device 900, according to embodiments of the present disclosure. FIG. 9 includes a front view 910 and a side view 920 of pin directing device 900. In addition, FIG. 9 includes a magnified front view 930 and a magnified side view 940 of a tip 902 of pin directing device 900.

The pin directing device 900 is generally used to direct an orthopedic device such as an intramedullary implant during orthopedic surgery. The orthopedic device may be, for example, a flexible bone screw or pin. The present disclosure will refer to direction of flexible bone screws, as an example, however other examples of orthopedic devices such as other intramedullary implants are also contemplated. A potential problem with the flexible bone screws is that, when multiple flexible bone screws are installed from the same entry hole, the threaded ends of the various flexible bone screws tend to cluster in a location dictated by the elasticity of the flexible bone screws and the anatomic shape of the intramedullary canal.

Figure 10:
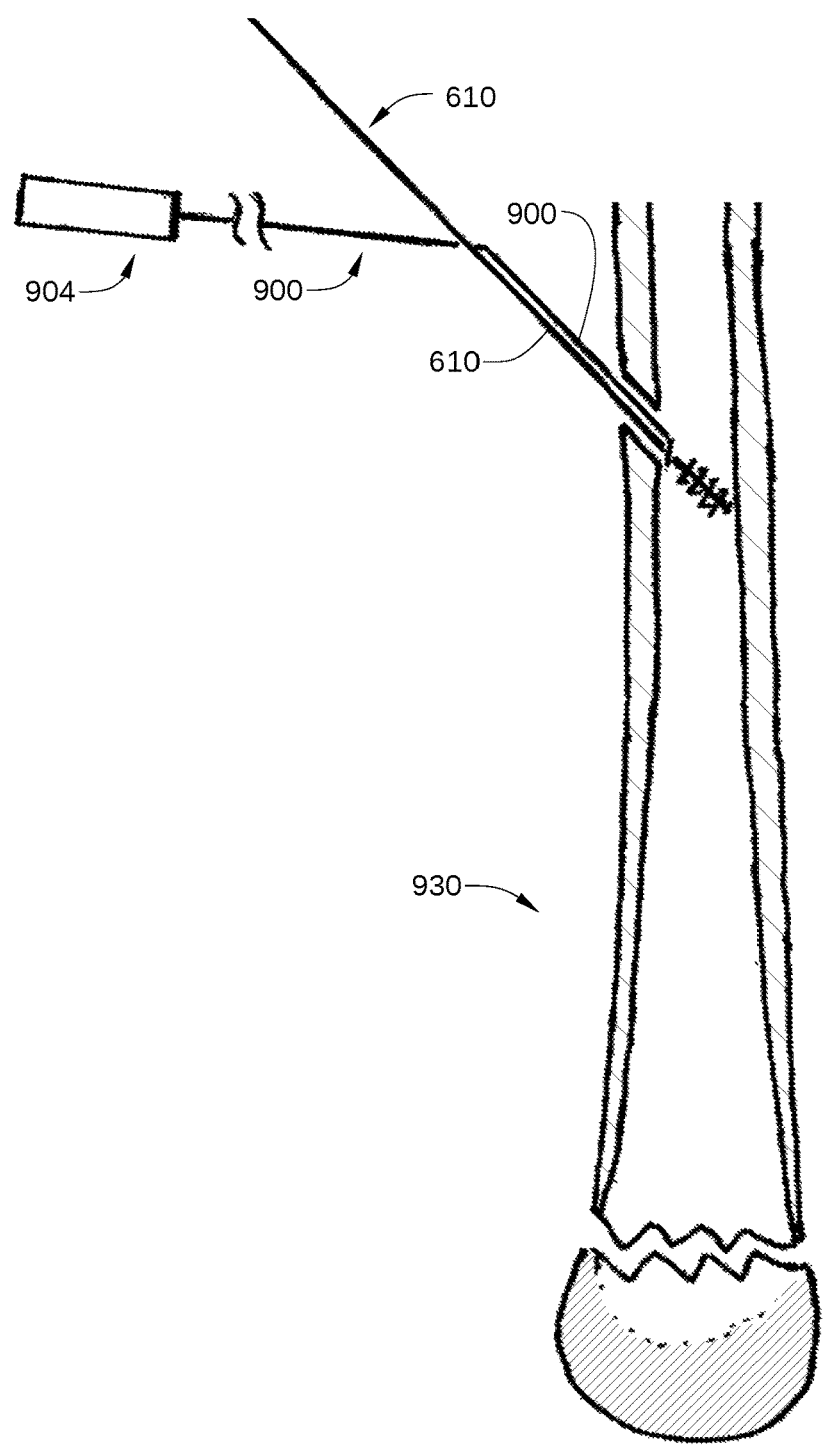
FIG. 10 is an illustration of a pin directing device slipped onto the shaft end of a flexible bone screw, according to an embodiment of the present disclosure.
Figure 11:
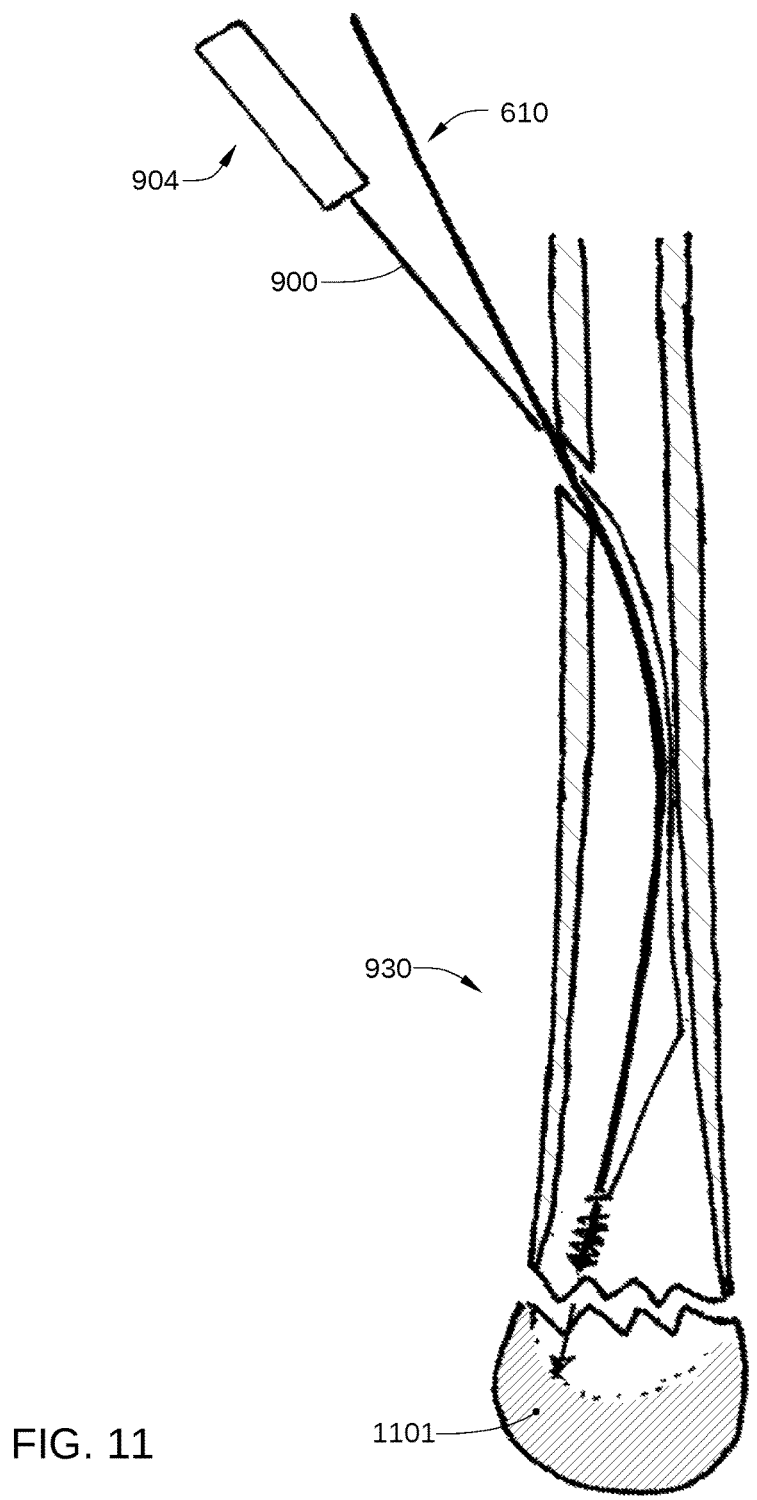
FIG. 11 is an illustration of a flexible bone screw and pin directing device passing through a hole in the cortex of the bone into the intramedullary space of the bone, according to an embodiment of the present disclosure.

The pin directing device 900 is generally elongate, thin, flexible and curved. The pin directing device 900 is approximately the length of the flexible bone screw, or other orthopedic device, which is to be directed inside the intramedullary canal. There is a hole 903 (or eyelet) at the tip 902 of the pin directing device 900. The passage length of the hole at the tip 902 may be very small or large relative to the length of the pin directing device 900. The hole at the tip 902 allows passage of the shaft of the flexible bone screw to be controlled and directed by moving the pin directing device 900. In one example, the hole at the tip 902 is formed through a very short segment of the far end of the pin directing device 900, forming an eyelet, and that far end is bent, such that after the shaft of the flexible bone screw passes through the small hole at the tip 902. More particularly, the hole at the tip 902 may be made with wire, such as 1.6 mm stainless steel wire, which is flatted at the tip and then either cold or hot forged to create an eyelet in the flattened portion. Alternatively, the tip is made by welding or brazing a separate loop of wire onto the tip of the pin directing device. This increases the strength and reduces fragility of the loop or eyelet, compared to an eyelet created by flattening the wire of the pin directing device, and then drilling a hole through this flat portion. See magnified side view 940. Additionally, bends in the pin directing device 900 may be created. For example, the pin directing device 900 may have a bend 911 adjacent to the hole in the tip allowing the shaft of the flexible bone screw to lie alongside of the adjacent shaft of the pin directing device 900. The pin directing device may also or alternatively have a bend 912 between 1 cm and 7 cm from the eyelet 903. The shaft of the flexible bone screw can lie substantially parallel to the shaft of the pin directing device 900, especially in the portion of the pin directing device shaft adjacent to the entry hole, as shown in FIG. 10. Generally, the first bend is located very close to the tip 902 of the pin directing device 900, for example within about 0 mm and 3 mm from the hole. There is a second bend approximately 1 to 7 cm from the far end hole or eyelet at the tip 902. This second bend serves as a fulcrum, so that the pin directing device 900 can lift the shaft of the flexible bone screw away from the far side of the intramedullary canal, and with twisting of the pin directing device shaft, the flexible bone screw can be manipulated into various locations within the intramedullary canal, as shown in FIG. 11. The near end of the pin directing device 900 projects from the entry hole in the bone, and the pin directing device 900 may be advanced into the hole or pulled back out of the hole. The near end may also be twisted clockwise or counterclockwise manipulating the position of the hole of the pin directing device 900 and the shaft of the flexible bone screw while observed under fluoroscopy. This allows the flexible bone screw to be efficiently and accurately directed. A handle (or other manual control means) 904 is placed on the near end of the pin directing device 900, so that the surgeon may grasp the handle 904 to facilitate advancing or withdrawing the pin directing device 900 from the intramedullary canal, and twisting the pin directing device 900.

One example of a method of operation of the pin directing device 900 is as follows. A hole is made in the cortex of a bone 930 with a bone entry tool such as a fluted trocar, an example of which is discussed below, or other drilling device. The pin directing device 900 is slipped onto the shaft end of the flexible bone screw and the hole and the tip 902 of the pin directing device 900 is slid all the way up against the wider thread end of the flexible bone screw, as shown in FIG. 10. The shaft of the pin directing device 900 is then tilted, such that the shaft of the pin directing device 900 adjacent to the tip 902 is lying parallel to the shaft of the flexible bone screw. As shown in FIG. 11, the flexible bone screw and pin directing device 900 are then passed through the hole in the cortex of the bone into the intramedullary space of the bone. Generally the transverse dimension of the hole or eyelet at the tip 902 of the pin directing device 900 is chosen to be smaller than the entry hole into the bone, or smaller than the thread major diameter at the tip of the flexible bone screw. The flexible bone screw is then advanced up the canal of the bone, e.g., by rotating it using a drill that is attached to the proximal end of the flexible bone screw, and the pin directing device 900 is pushed to follow immediately behind it. The flexible bone screw is advanced up the bone, into the zone of cancellous bone near the end of the bone, and at this time the pin directing device 900 is manipulated to steer the tip of the flexible bone screw, so that the threaded tip of the flexible bone screw enters the cancellous bone 1101 in a preferred location. This is observed and directed under fluoroscopy. The flexible bone screw is then twisted and threadedly advanced into the cancellous bone in the location targeted under fluoroscopic imaging, without pushing the pin directing device 900 behind it. The pin directing device 900 is now extracted from the intramedullary cavity by pulling on it and twisting. The twisting, by for example ½ turn, may be necessary to extract the pin directing device 900, especially as it is sliding over the shaft of the flexible bone screw, where the shaft is coming out of the hole in the side of the bone. The pin directing device 900 may be twisted such that the shaft of the pin directing device 900 is sitting on top of the shaft of the flexible bone screw and nearly parallel to the flexible bone screw, facing the surgeon, and it is pulled out of the cortex hole in this rotational position. This allows the pin directing device 900 to act as a sled against the cortical bone, and prevents the hole or eyelet at the tip 902 of the pin directing device 900 from becoming hooked against the cortex at the hole in the bone. If the hole of the pin directing device 900 does become hooked against the cortical bone at the entry hole, the pin directing device 900 maybe twisted and pulled harder, and this will result in breakage of the hole through a notch 906 (shown in FIG. 9) at the most distal extent of the hole or eyelet, as shown in FIG. 1D. The hole at the tip 902 of the pin directing device 900 may also become hooked at other sites inside the bone as well. The breakage of the hole at the tip 902 occurs in a controlled and planned fashion at the frangible notch 906. The notch 906 is preferably at the most distal extent of the hole at the tip 902, allowing the hole to open at the frangible notch in the ring of the hole at the tip 902, with spreading of both sides of the hole or eyelet. This allows spreading and opening of the ring of the hole, and extraction of the pin directing device 900 out of the intramedullary space, allow without leaving a small fragment of metal from the pin directing device 900. In another example, the hole may not include a notch 906.

The pin directing device 900, which includes a steering handle 904, an elongate shaft, and a tip 902 having a hole therethrough, allows a user, such as a doctor, to direct and control the movement of a flexible bone screw, or other orthopedic device, through the cavity of a bone while the flexible bone screw is steered and advanced through the length of the bone by a motor drill unit. Additionally, the frangible notch 906 of the pin directing device 900 allows extraction from the bone without sliding the pin directing device 900 off the shaft of the flexible bone screw, even if the hole in the tip 902 becomes hooked within the bone.

In some embodiments, a pin directing device comprises an elongated shaft; a tip at a distal end of the elongated shaft having a hole therein for engaging a flexible bone screw; and a handle at a proximal end of the elongated shaft configured to be rotated to advance, retract, or steer the flexible bone screw through an intramedullary cavity. In some embodiment, the hole at the tip of the distal end is an eyelet. In some embodiments, the pin directing device has first a bend adjacent to the eyelet allowing a shaft of the flexible bone screw to lie alongside of an adjacent shaft of the pin directing device. In some embodiments, the pin directing device has a second bend between about 1 cm and about 7 cm from the eyelet. In some embodiments, the elongated shaft is thin such that a diameter of the elongated shaft is less than an entry hole diameter minus a diameter of the shaft of the flexible bone screw.

Flexible Bone Screw with a Rotary Position Marker

After insertion of a flexible bone screw, or other orthopedic device, into a bone canal, it is difficult to know the rotary position of the tip of the flexible bone screw which is inside the bone canal without viewing it using fluoroscopic imaging. Even with fluoroscopy, however, the determined rotary position of the tip is not always accurate.

Figure 12:
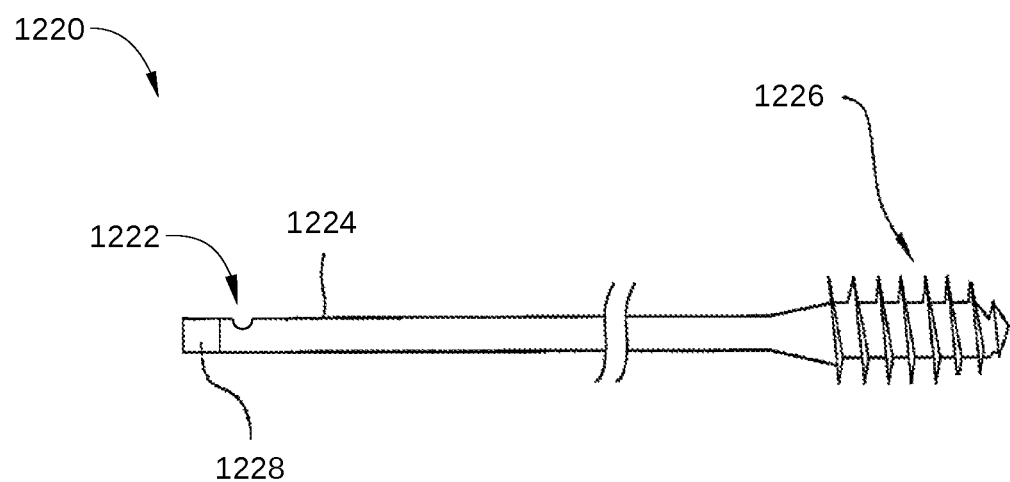
FIG. 12 is a flexible bone screw with a rotary position marker, according to an embodiment of the present disclosure.

FIG. 12 is a flexible bone screw 1220 with a rotary position marker 1222 according to the present disclosure. The flexible bone screw 1220 is configured for management of proximal humerus fractures. The flexible bone screw 1220 includes a shaft 1224, a threaded portion 1226, and a tool engagement portion 1228. In some embodiments, tool engagement portion 1228 may be any suitable length that is less than approximately half the length of shaft 1224. Thus, in some embodiments, tool engagement portion 1228 can extend beyond In one example, the rotary position marker 1222 may be a groove or mark 1222 milled onto the side of the shaft 1224, for example, in the 25% terminal portion of the shaft 1224. In another example, the rotary position marker 1222 may be a laser etched mark on the side of the shaft 1224, for example, in the extent of the shaft 1224 25% from the end. In another example, the rotary position marker 1222 may be a surface ground onto the side of the shaft 1224 at a similar position near the end. In yet another example, the rotary position marker 1222 may be a cold forged mark on the side of the shaft 1224, for example, in the terminal 25% of the shaft 1224. In yet other examples, the rotary position marker 1222 may be a non-axisymmetric grind on the end of the shaft, or a small bend at the end of the shaft.

In operation, a flexible bone screw 1220 is used to stabilize a fracture. Then, on intraoperative radiographic images, it may be noted that the fracture site is angulated in an unacceptable way. The angulation is in one direction, for example, apex medial. The flexible bone screw 1220 is withdrawn from the bone, and at the level of the fracture, the shaft 1224 of the flexible bone screw 1220 is bent to an angle necessary to correct the improper angulation of the fracture. The user may reference the rotary position marker 1222 on the shaft 1224 for the direction of the apex of the bend. The flexible bone screw 1220 is then re-inserted, and advanced up the bone until the rotary position marker 1222 is directed laterally, thereby correcting the apex medial angulation.

The rotary position marker 1222 may be used to determine the rotary position of the tip of the flexible bone screw 1220 that is inside the bone without relying completely on fluoroscopy or other intraoperative imaging. One occasion when rotary position of the tip is important is when there is a bend in the shaft of the flexible bone screw 1220. A bend in the shaft may be introduced to correct for angular position of a fracture that the shaft of the flexible bone screw is crossing over. Decreased imaging radiation may be achieved using the flexible bone screw 1220 with a rotary position marker 1222 without use of fluoroscopy.

In some embodiments, a flexible bone screw comprises an elongated shaft that is configured for elastic bending having a rotational position marker positioned thereon at a terminal twenty-five percent of the shaft; and a threaded portion at one end of the shaft for engagement with a bone, the threaded portion having an outer diameter that is larger than a diameter of the shaft.

Side Application Bending Clamp

After insertion of a flexible bone screw, or other orthopedic device, into a bone, it is often either desirable, or necessary to cut off the extra length of the proximal end of the flexible bone screw that projects out of the bone. The cut end of the flexible bone screw may be sharp and palpable under the skin after the wound is closed. It is therefore desirable to have a technique by which the flexible bone screw that has been cut off can be bent over so that there is a smooth knuckle under the skin and the sharp end of the flexible bone screw does not poke against the skin. It is known that short ends of stiff metal bone screws and shafts of bone screws are bent with considerable difficulty using standard operating room instruments. Standard plate and pin bending irons do not work well because they have difficulty grabbing a short bone screw, and they spin and rotate while trying to bend.

Figure 13A:
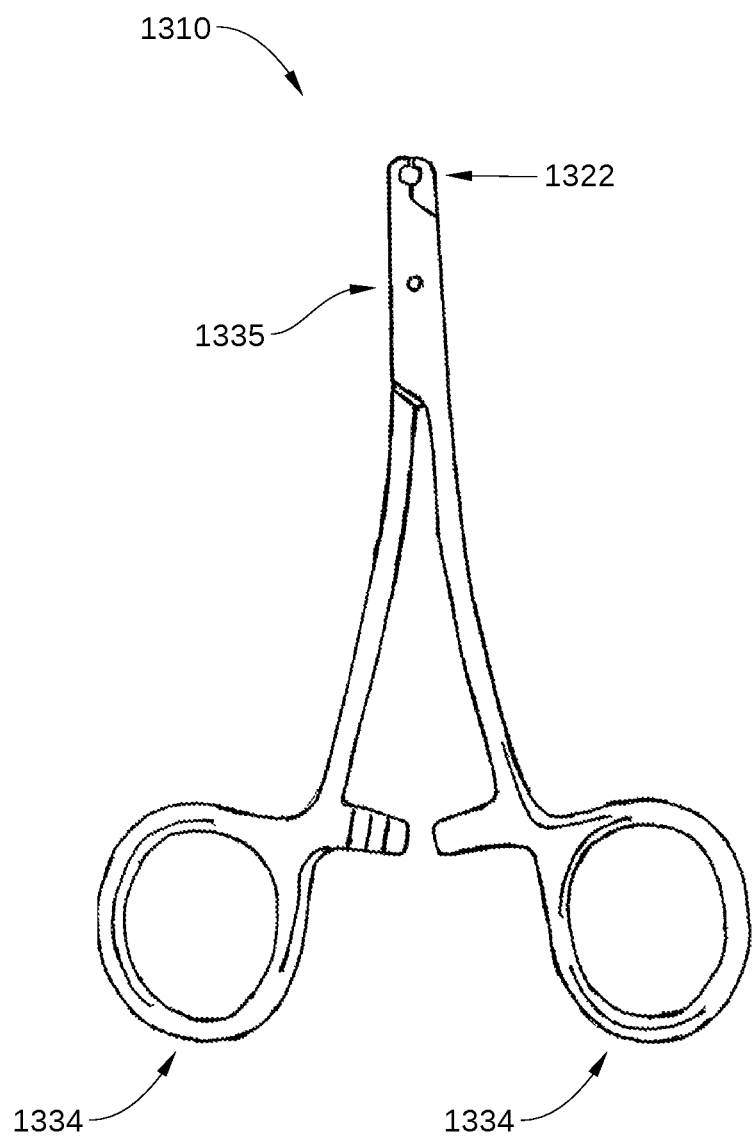
FIGS. 13A is a view of one bending tool of a pair of bending tools that make up a pin bending clamp, according to embodiments of the present disclosure.
Figure 13B:
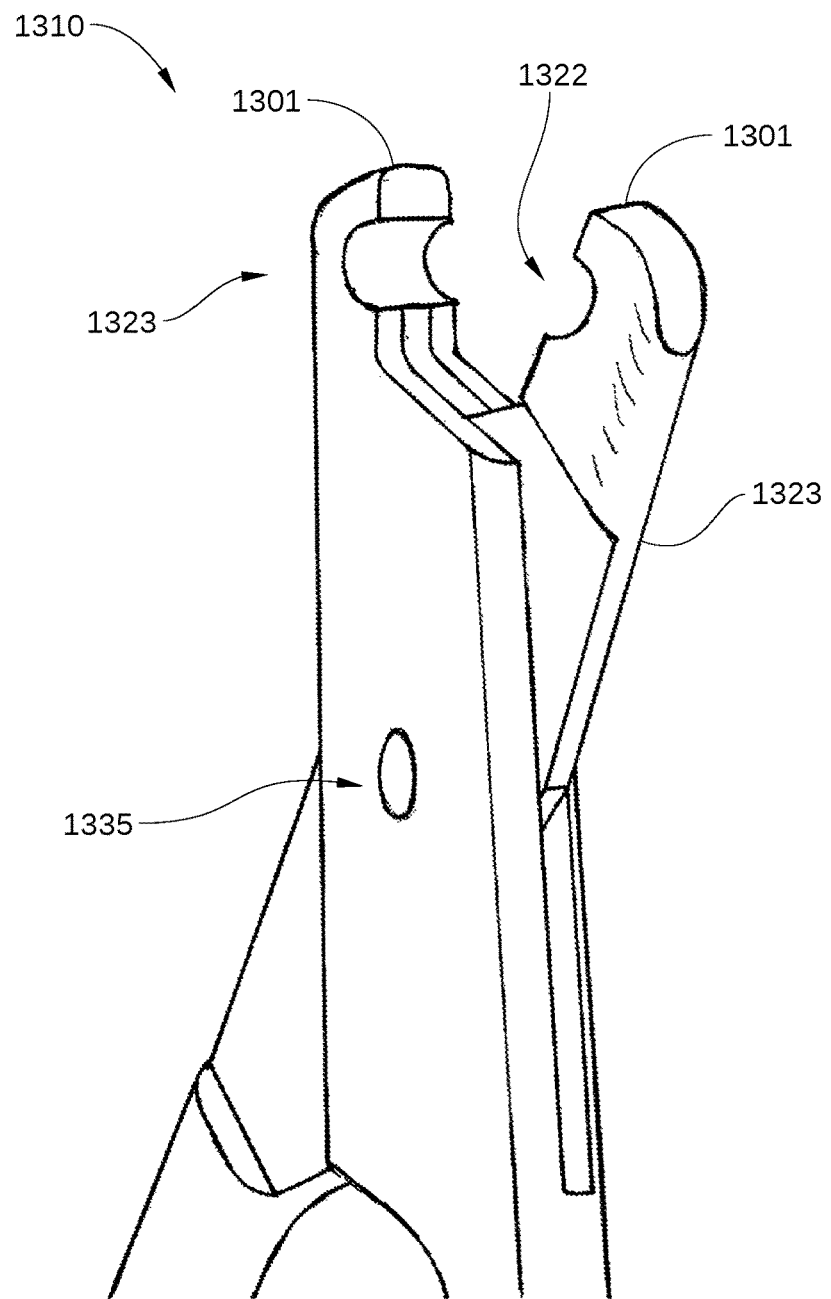
FIG. 13B is a close-up view of the tips of one bending tool, according to embodiments of the present disclosure.
Figure 13C:
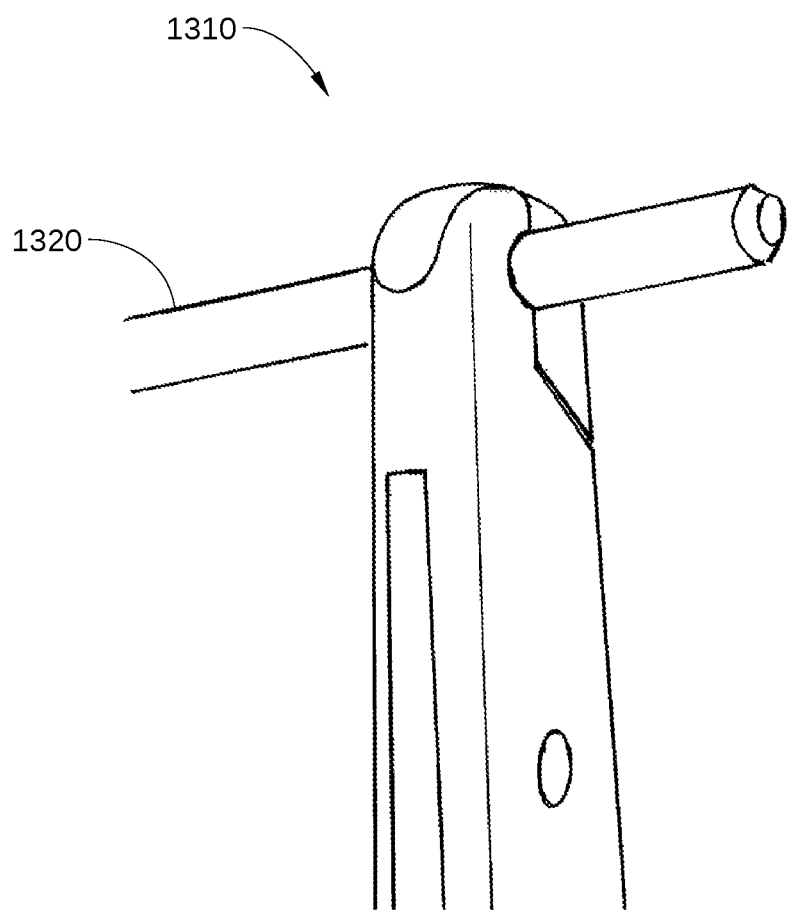
FIG. 13C is a view of one bending tool of a pin bending clamp holding a shaft of a flexible bone screw, according to embodiments of the present disclosure.
Figure 13D:
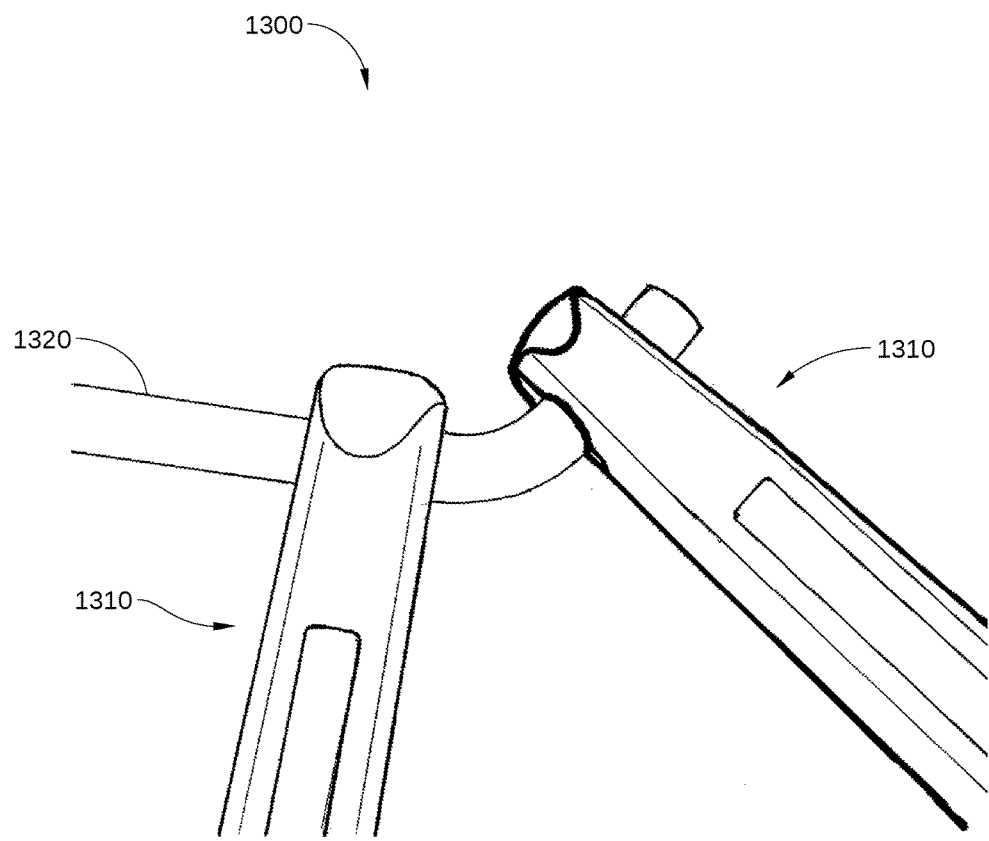
FIG. 13D is a view of a pin bending clamp being used to bend a shaft of a flexible bone screw, according to embodiments of the present disclosure.

FIGS. 13A is a view of one bending tool 1310 of a pair of bending tools that make up a pin bending clamp, according to embodiments of the present disclosure. FIG. 13B is a close-up view of tips 1301 of one bending tool 1310 according to embodiments of the present disclosure. FIG. 13C is a view of one bending tool 1310 of pin bending clamp 1300 holding a shaft 1320 of a flexible bone screw, according to embodiments of the present disclosure. FIG. 13D is a view of pin bending clamp 1300 being used to bend a shaft 1330 of a flexible bone screw, according to embodiments of the present disclosure.

The pin bending clamp 1300 may include a pair of bending tools 1310, each having a transverse hole 1322 (shown in FIGS. 13A and 13B) near tips 1301. Each transverse hole 1322 is located in bending tool 1310 to intersect with the inner surface of the bending tool 1310. Thus, when the bending too 1310 is open, the hole space is open. The bending tool 1301 closes with closure of jaws 1323, which are located opposite a hinge 1335 from handles 1334. The transverse holes 1322 are generally approximately equal to the diameter of the shaft of the flexible bone screw to be bent. Each of the bending tools has handles 1334 which, when moved apart, open the jaws of the bending tool 1301, and allow the shaft of the flexible bone screw to be placed into the transverse hole 1322 in jaws 1323 of the bending tool 1301. Thus, the shaft of the flexible bone screw may be engaged by opening jaws 1323, approaching from the side, and then closing over the shaft, achieving a firm hold onto the shaft.

In operation, as shown in FIGS. 13C and 13D, a proximal end of the flexible bone screw, before or after cutting, is grasped by a bending clamp 1310. The handle 1334 is locked in the clamped position. The handle 1334 is then moved in the plane shared by the bending clamp and the shaft, introducing a bend in the shaft. This procedure may be performed with a pair of bending tools 1310 side-by-side, moving the bending tool 1301 that is closer to the shaft end, introducing a bend at a location in the shaft between the two bending tools 1301. Generally the shaft end is bent in a direction away from the skin surface, providing a smooth knuckle of wire under the skin that is not aggravating to a patient with such an orthopedic device.

While the foregoing is directed to implementations with flexible bone screws in several examples, other orthopedic devices and applications, such as pins or other screws or other screws, may be devised without departing from the basic scope thereof.

In some embodiments, a pin bending device comprises a clamp comprising a hinged instrument with two handles, a hinge, and two jaws located opposite the hinge from the handles. In some embodiments, the pin bending device comprises a handle that is disposed at a proximal end of each of the bending tools. In some embodiments, a recess in the jaws of the clamp receives the shaft of the flexible bone screw, said recess communicating with the closing surface of the jaws.

Bone Screw Application Kit

A kit for application of the flexible bone screw is further developed. The kit consists of multiple flexible bone screws and at least an entry tool. The it may include three, four, or five flexible bone screws. Additionally it may include a Bending Clamp. Additionally it may also include a steering device.

The method of application of the flexible bone screw includes first making an entry hole in the side of the bone with the entry tool. Optionally at this time the shaft of the flexible bone screw may be inserted through the eyelet of the steering device. The flexible bone screw is then mounted in a motorized driver, and inserted into the entry hole in the bone. The threaded tip of the flexible screw is then run with motorized rotation against the far cortex, allowing it to climb the far cortex and bend, moving along the intramedullary canal. The fracture is reduced under fluoroscopic imaging, and then the flexible bone screw is run across the fracture, with or without guidance from the steering device, and into the cancellous bone of the opposing bone fragment. This process is repeated with additional screws as needed, until sufficient stability of the fracture has been achieved. The excess length of the shafts may then be cut off, and the ends of the shafts protruding from the bone may be bent with the bending clamp.

In some embodiments, a bone fracture repair device comprises a flexible bone screw having an elongated shaft that is configured for elastic bending with a thread at one end; and a cortex climbing thread portion at one end of the flexible bone screw, wherein the cortex climbing thread portion is substantially helicoid and an aperture angle of a cone containing the cortex climbing thread portion is 90 degrees or more, wherein the cortex climbing thread portion has an end view surface area less than 20 percent being part of a surface of revolution, and wherein the cortex climbing thread portion is configured to rotationally climb up an inside of a tubular bone cortex and penetrate cancellous bone.

While the foregoing is directed to embodiments of the present invention, other and further embodiments of the invention may be devised without departing from the basic scope thereof, and the scope thereof is determined by the claims that follow.

What is claimed is:

1. A threaded orthopedic device, comprising:
 a flexible shaft; and
 a threaded portion that is disposed on one end of the shaft, wherein the threaded portion includes a tip region with a tip thread, a body portion with a body thread that has a major diameter that is equal to or greater than the largest major diameter of the tip thread, and a transition point disposed where an edge surface of the tip thread meets an edge surface of the body thread,
 wherein the tip region is disposed entirely within a cone that is 1) centered on a longitudinal axis of the shaft and 2) passes through the transition point, such that no part of the tip region protrudes through a surface of the cone, and
 wherein an aperture angle of the cone is between 45 degrees and 120 degrees.

2. The threaded orthopedic device of claim 1, wherein an aperture angle of the cone is 90 degrees.

3. The threaded orthopedic device of claim 1, wherein an aperture angle of the cone is 45 degrees.

4. The threaded orthopedic device of claim 1, wherein an aperture angle of the cone is 120 degrees.

5. The threaded orthopedic device of claim 1, wherein the body portion is contained within a cylinder having walls that contact edges of the body thread.

6. The threaded orthopedic device of claim 5, wherein the cylinder has a diameter that is equal to the major diameter of the body thread.

7. The threaded orthopedic device of claim 1, wherein the body portion is contained within a rotational body having walls that contact edges of the body thread.

8. The threaded orthopedic device of claim 7, wherein the walls of the rotational body is tapered towards the tip region.

9. The threaded orthopedic device of claim 1, wherein the tip region has helicoid surfaces.

10. The threaded orthopedic device of claim 9, wherein each of the helicoid surfaces forms an angle that is closer to perpendicular with respect to the longitudinal axis of the shaft than that formed by the surface of the cone with respect to the longitudinal axis of the shaft.

11. The threaded orthopedic device of claim 9, wherein a core diameter of the tip region decreases towards a tip of the tip region.

12. The threaded orthopedic device of claim 1, wherein the flexible shaft is made from a metal that is cold-worked.

13. The threaded orthopedic device of claim 1, wherein the flexible shaft is made from a metal alloy that is cold-worked.

14. The threaded orthopedic device of claim 1, wherein the flexible shaft is made from stainless steel that is cold-worked.

* * * * *